United States Patent
Hanaoka et al.

(10) Patent No.: US 7,141,690 B2
(45) Date of Patent: Nov. 28, 2006

(54) TRANSITION METAL COMPLEXES, LIGANDS, POLYMERIZATION CATALYSTS FOR OLEFINS, AND PROCESS FOR PRODUCTION OF OLEFIN POLYMERS

(75) Inventors: Hidenori Hanaoka, Suita (JP); Taichi Senda, Toyonaka (JP); Eiji Yoshikawa, Ibaraki (JP); Satoshi Kobayashi, Tsukuba (JP)

(73) Assignee: Sumitomo Chemical Company, Limited, Osaka (JP)

( * ) Notice: Subject to any disclaimer, the term of this patent is extended or adjusted under 35 U.S.C. 154(b) by 76 days.

(21) Appl. No.: 10/503,252

(22) PCT Filed: Feb. 6, 2003

(86) PCT No.: PCT/JP03/01215

§ 371 (c)(1),
(2), (4) Date: Aug. 3, 2004

(87) PCT Pub. No.: WO03/066641

PCT Pub. Date: Aug. 14, 2003

(65) Prior Publication Data

US 2005/0154158 A1    Jul. 14, 2005

(30) Foreign Application Priority Data

Feb. 8, 2002    (JP)    ............... 2002-032560

(51) Int. Cl.
*C08F 4/64*    (2006.01)
*C07F 7/28*    (2006.01)
*C07F 7/00*    (2006.01)

(52) U.S. Cl. .................. 556/52; 556/11; 556/12; 502/103; 502/128; 502/152; 502/158; 526/127; 526/133; 526/160; 526/165; 526/172; 526/943

(58) Field of Classification Search .................. 556/11, 556/12, 52; 502/103, 128, 152, 158; 526/127, 526/133, 160, 172, 943, 165
See application file for complete search history.

(56) References Cited

U.S. PATENT DOCUMENTS

| 6,187,889 B1 * | 2/2001 | Oi et al. ...................... 526/347 |
| 6,288,191 B1 * | 9/2001 | Nishiyama et al. .......... 526/339 |
| 6,329,478 B1 | 12/2001 | Katayama et al. ........... 526/127 |
| 6,632,541 B1 * | 10/2003 | Johoji et al. ................ 428/474.4 |

FOREIGN PATENT DOCUMENTS

| EP | 842939 | 5/1998 |
| WO | 98/06727 | 2/1998 |
| WO | 98/06728 | 2/1998 |
| WO | 99/24446 | 5/1999 |
| WO | 99/42467 | 8/1999 |
| WO | 00/66596 | 11/2000 |
| WO | 01/53360 | 1/2001 |
| WO | 01/42315 | 6/2001 |
| WO | 01/47939 | 7/2001 |
| WO | 01/48039 | 7/2001 |
| WO | 01/53361 | 7/2001 |

OTHER PUBLICATIONS

D.A. Kissounko et al., "Cyclopenta[b]thienyl ligand in organometallic chemistry. Studies of the regioselectivity of the synthesis of new σ-element-substituted cyclopenta[b]thiophene derivatives", Russian Chemical Bulletin, vol. 49, No. 7, pp. 1282-1286, 2000.
J. Klosin et al., "Heteroatom-Substituted Constrained-Geometry Complexes. Dramatic Substituent Effect on Catalyst Efficiency and Polymer Molecular Weight", Organometallics, vol. 20, No. 13, pp. 2663-2665, 2001.
J. A. Ewen et al., "Polymerization Catalysts with Cyclopentadienyl Ligands Ring-Fused to Pyrrole and Thiophene Heterocycles", J. Am. Chem. Soc., vol. 120, No. 41, pp. 10786-10787, 1998.
Russian Chemical Bulletin (Translation of Izvestiya Akademii Nauk, Seriya Khimicheskaya), vol. 49, No. 7, pp. 1282-1286, 2000.
J. A. Ewen et al., "Chiral *Ansa* Metallocenes with Cp Ring-Fused to Thiophenes and Pyrroles: Syntheses, Crystal Structures, and Isotactic Polypropylene Catalysts", J. Am. Chem. Soc., vol. 123, No. 20, pp. 4763-4773, 2001.

* cited by examiner

*Primary Examiner*—Caixia Lu
(74) *Attorney, Agent, or Firm*—Wenderoth, Lind & Ponack, L.L.P.

(57) ABSTRACT

A transition metal complex represented by the formula (1):

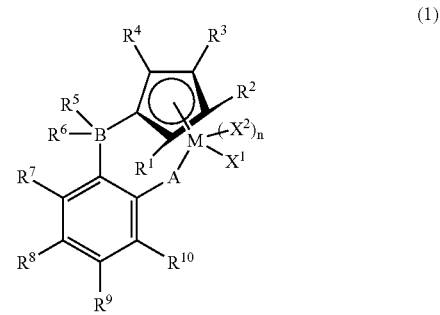

wherein M is a Group 4 transition metal, A is a Group 16 element, B is a Group 14 element, n is an integer of 0 or 1, $R^1$, $R^2$, $R^3$ and $R^4$ may be the same or different and each independently denotes a substituent selected from the group consisting of the groups (I) and (II):
  group (I): hydrogen, alkyl and so on,
  group (II): alkoxy, alkylthio and so on,
provided that at least one of $R^1$, $R^2$, $R^3$ and $R^4$ is a substituent selected from group (II);
$R^5$, $R^6$, $R^7$, $R^8$, $R^9$, $R^{10}$, $X^1$ and $X^2$ may be the same or different and are each hydrogen, halogen, alkyd or the like; and a catalyst for olefin polymerization comprising said complex, an organoaluminum compound and a boron compound are provided.

18 Claims, No Drawings

TRANSITION METAL COMPLEXES, LIGANDS, POLYMERIZATION CATALYSTS FOR OLEFINS, AND PROCESS FOR PRODUCTION OF OLEFIN POLYMERS

This application is a U.S. national stage of International Application No. PCT/JP03/01215 filed Feb. 6, 2003.

TECHNICAL FIELD

The present invention relates to transition metal complexes, ligands, catalysts for olefin polymerization, and process for production of olefin polymers.

BACKGROUND ART

Many production methods of olefin polymers by using metallocene complexes have already been reported. For example, JP-A 58-19309 disclosed a method of producing olefin polymers using a metallocene complex and aluminoxane. However, such a method, in which olefin polymerization is carried out catalytically by using bis(cyclopentadienyl)zirconium dichloride and methylaluminoxane, had a problem of the low molecular weight of the obtained olefin polymer. To resolve the problem, JP-A 9-87313 disclosed polymerization using dimethylsilyl(tetramethylcyclopentadienyl)(3-tert-butyl-5-methyl-2-phenoxy)titanium dichloride. In such polymerization, the catalytic activity is high, but there is still a need for further improvement in the molecular weights of polymers to be obtained.

DISCLOSURE OF THE INVENTION

In consideration of the above-mentioned problems, the present invention aims to provide transition metal complexes with excellent catalytic activity and capable of providing polymers with high molecular weight, and a process of producing olefin polymers using them.

In order to accomplish the above-mentioned aims, the present inventors had made investigations on transition metal complexes and catalysts for olefin polymerization, and finally found transition metal complexes having ligands comprising a cyclopentadiene ring having a heteroatom as a substituent and which ring is connected with a substituted benzene ring via a covalent bond group, thereby the present invention was accomplished.

That is, the invention provides as follows:
1. a transition metal complex represented by the formula (1)

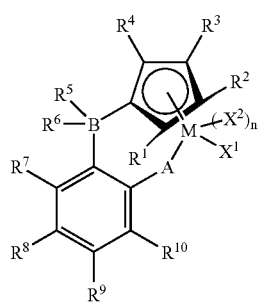

(1)

wherein M is a Group 4 transition metal;
A is a Group 16 element;
B is a Group 14 element;
n is an integer of 0 or 1;
$R^1$, $R^2$, $R^3$ and $R^4$ are the same or different and each independently denotes a substituent selected from the group consisting of the following groups (I) and (II):

group (I) consisting of
hydrogen,
substituted or unsubstituted $C_{1-20}$ alkyl,
substituted or unsubstituted $C_{6-20}$ aryl,
substituted or unsubstituted $C_{7-20}$ aralkyl, and
silyl substituted with substituted or unsubstituted $C_{1-20}$ hydrocarbon, and group (II) consisting of
substituted or unsubstituted $C_{1-20}$ alkoxyl,
substituted or unsubstituted $C_{6-20}$ aryloxy,
substituted or unsubstituted $C_{7-20}$ aralkyloxy,
silyloxy substituted with substituted or unsubstituted $C_{1-20}$ hydrocarbon,
amino substituted with substituted or unsubstituted $C_{1-20}$ hydrocarbon,
phosphino substituted with substituted or unsubstituted $C_{1-20}$ hydrocarbon, and
thio substituted with substituted or unsubstituted $C_{1-20}$ hydrocarbon,
provided that at least one of $R^1$, $R^2$, $R^3$ and $R^4$ is a substituent group selected from the group (II);

$R^5$, $R^6$, $R^7$, $R^8$, $R^9$ and $R^{10}$ are the same or different and each independently denotes hydrogen, halogen,
substituted or unsubstituted $C_{1-20}$ alkyl,
substituted or unsubstituted $C_{1-20}$ alkoxy,
substituted or unsubstituted $C_{6-20}$ aryl,
substituted or unsubstituted $C_{6-20}$ aryloxy,
substituted or unsubstituted $C_{7-20}$ aralkyl,
substituted or unsubstituted $C_{7-20}$ aralkyloxy,
silyl substituted with substituted or unsubstituted $C_{1-20}$ hydrocarbon, or
amino substituted with substituted or unsubstituted $C_{1-20}$ hydrocarbon; and $X^1$ and $X^2$ are the same or different and each independently denotes hydrogen, halogen,
substituted or unsubstituted $C_{1-20}$ alkyl,
substituted or unsubstituted $C_{1-20}$ alkoxy,
substituted or unsubstituted $C_{6-20}$ aryl,
substituted or unsubstituted $C_{6-20}$ aryloxy,
substituted or unsubstituted $C_{7-20}$ aralkyl,
substituted or unsubstituted $C_{7-20}$ aralkyloxy, or
amino substituted with substituted or unsubstituted $C_{1-20}$ hydrocarbon; or two adjacent substituents of $R^1$, $R^2$, $R^3$ and $R^4$, and two adjacent substituents of $R^5$, $R^6$, $R^7$, $R^8$, $R^9$ and $R^{10}$ may be each optionally bonded to form a ring;

2. a process of producing a transition metal complex represented by the formula (1) which comprises reacting substituted cyclopentadiene represented by the formula (2):

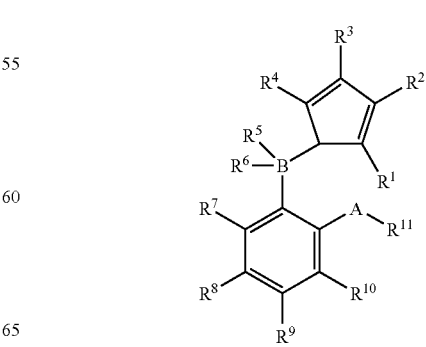

(2)

wherein A, B, $R^1$, $R^2$, $R^3$, $R^4$, $R^5$, $R^6$, $R^7$, $R^8$, $R^9$ and $R^{10}$ are as defined above, and $R^{11}$ is a substituted or unsubstituted hydrocarbon group or a trisubstituted silyl group, and the positions of the double bonds on the cyclopentadiene ring are optional or be a mixture of optional positions; with a base and then reacting with a transition metal compound represented by the formula (3):

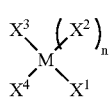
(3)

wherein M and n are as defined above;

$X^1$, $X^2$, $X^3$ and $X^4$ are the same or different and each independently denotes hydrogen, halogen, substituted or unsubstituted $C_{1-20}$ alkyl, substituted or unsubstituted $C_{1-20}$ alkoxy, substituted or unsubstituted $C_{6-20}$ aryl, substituted or unsubstituted $C_{6-20}$ aryloxy, substituted or unsubstituted $C_{7-20}$ aralkyl, substituted or unsubstituted $C_{7-20}$ aralkyloxy, or amino substituted with substituted or unsubstituted $C_{1-20}$ hydrocarbon;

3. substituted cyclopentadiene represented by the above-mentioned formula (2);

4. a process of producing substituted cyclopentadiene represented by the above-mentioned formula (2) which comprises reacting substituted cyclopentadiene represented by the formula (5):

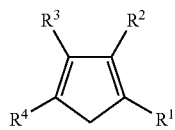
(5)

wherein $R^1$, $R^2$, $R^3$ and $R^4$ are as defined above, with a base and then reacting with a compound represented by the formula (6):

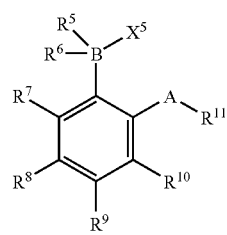
(6)

wherein $X^5$ is halogen and A, B, $R^5$, $R^6$, $R^7$, $R^8$, $R^9$, $R^{10}$ and $R^{11}$ are as defined above;

5. substituted cyclopentadiene represented by the above-mentioned formula (4):

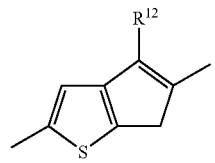
(4)

wherein $R^{12}$ is hydrogen, substituted or unsubstituted $C_{1-20}$ alkyl or substituted or unsubstituted $C_{6-20}$ aryl;

6. a catalyst for olefin polymerization comprising a transition metal complex represented by the above-mentioned formula (1) in combination with the following compound (A), wherein (A) is any one of or a mixture of two or three of the following compounds (A1) to (A3):

(A1): an organoaluminum compound represented by the formula $E1_a Al(Z)_{(3-a)}$, (A2): cyclic aluminoxane having the structure represented by the formula $\{-Al(E2)-O-\}_b$, (A3): linear aluminoxane having the structure represented by the formula $E3\{-Al(E3)-O-\}_c Al(E3)_2$, wherein E1 to E3 are the same or different and each independently denotes a $C_{1-8}$ hydrocarbon group, Z is the same or different and each denotes hydrogen or halogen, a is an integer of 1, 2 or 3, b is an integer of 2 or more, and c is an integer of 1 or more;

7. a catalyst of olefin polymerization comprising the transition metal complex represented by the above-mentioned formula (1) in combination with the following compounds (A) and (B), wherein (A) is any one of or a mixture of two or three of the following compounds (A1) to (A3):

(A1): an organoaluminum compound represented by the formula $E1_a Al(Z)_{(3-a)}$, (A2): cyclic aluminoxane having the structure represented by the formula $\{-Al(E2)-O-\}_b$, (A3): linear aluminoxane having the structure represented by the formula $E3\{-Al(E3)-O-\}_c Al(E3)_2$, wherein E1 to E3 are the same or different and each independently denotes a $C_{1-8}$ hydrocarbon group, Z is the same or different and each denotes hydrogen or halogen, a is an integer of 1, 2 or 3, b is an integer of 2 or more, and c is an integer of 1 or more, and (B) is any one of or a mixture of two or three of the following compounds (B1) to (B3):

(B1): a boron compound represented by the formula BQ1Q2Q3, (B2): a boron compound represented by the formula $Z^+(BQ1Q2Q3Q4)^-$, (B3): a boron compound represented by the formula $(L-H)^+(BQ1Q2Q3Q4)^-$, wherein B is a boron atom in a trivalent valence state, Q1 to Q4 are the same or different and each is a halogen atom, a $C_{1-20}$ hydrocarbon group, a $C_{1-20}$ halogenated hydrocarbon group, a substituted silyl group having 1 to 20 carbon atoms, a $C_{1-20}$ alkoxy group or a disubstituted amino group having 2–20 carbon atoms, and L-H is a Brønsted acid; and 8. a process of producing an olefin polymer which comprises polymerizing olefin in the presence of the catalyst for olefin polymerization as described in the above 6 or 7.

MODE FOR CARRYING OUT THE INVENTION

Hereinafter, the present invention will be described in details.

With respect to transition metal complexes represented by the formula (1), the transition metal atom denoted by M is a Group 4 transition metal atom in the periodic table (IUPAC Inorganic Chemical Nomenclature revised in 1989) and it is, for example, a titanium atom, a zirconium atom or a hafnium atom and preferably a titanium atom.

The element denoted by A is a Group 16 element in the periodic table and it is, for example, an oxygen atom, a sulfur atom or a selenium atom and preferably an oxygen atom.

The element denoted by B is a Group 14 element in the periodic table and it is, for example, a carbon atom, a silicon atom or a germanium atom and preferably a silicon atom.

n denotes an integer of 0 or 1 and preferably 1.

The halogen atom denoted by $R^1$, $R^2$, $R^3$, $R^4$, $R^5$, $R^6$, $R^7$, $R^8$, $R^9$, $R^{10}$, $X^1$ and $X^2$ include a fluorine atom, a chlorine atom, a bromine atom and an iodine atom and a chlorine atom is preferably exemplified.

A substituent for the substituted $C_{1-20}$ alkyl denoted by $R^1$, $R^2$, $R^3$, $R^4$, $R^5$, $R^6$, $R^7$, $R^8$, $R^9$, $R^{10}$, $X^1$ and $X^2$ includes halogen atoms. Specific examples of the substituted or unsubstituted alkyl include, for example, methyl, ethyl, n-propyl, isopropyl, n-butyl, sec-butyl, tert-butyl, n-pentyl, neopentyl, amyl, n-hexyl, heptyl, n-octyl, n-nonyl, n-decyl, n-dodecyl, n-tridecyl, tetradecyl, pentadecyl, hexadecyl, heptadecyl, octadecyl, nonadecyl, n-eicosyl, fluoromethyl, difluoromethyl, trifluoromethyl, chloromethyl, dichloromethyl, trichloromethyl, bromomethyl, dibromomethyl, tribromomethyl, iodomethyl, diiodomethyl, triiodomethyl, fluoroethyl, difluoroethyl, trifluoroethyl, tetrafluoroethyl, pentafluoroethyl, chloroethyl, dichloroethyl, trichloroethyl, tetrachloroethyl, pentachloroethyl, bromoethyl, dibromoethyl, tribromoethyl, tetrabromoethyl, pentabromoethyl, perfluoropropyl, perfluorobutyl, perfluoropentyl, perfluorohexyl, perfluorooctyl, perfluorododecyl, perfluoropentadecyl, perfluoroeicosyl, perchloropropyl, perchlorobutyl, perchloropentyl, perchlorohexyl, perchlorooctyl, perchlorododecyl, perchloropentadecyl, perchloroeicosyl, perbromopropyl, perbromobutyl, perbromopentyl, perbromohexyl, perbromooctyl, perbromododecyl, perbromopentadecyl and perbromoeicosyl and the preferable examples are methyl, ethyl, isopropyl, tert-butyl and amyl.

A substituent for the substituted $C_{7-20}$ aralkyl denoted by $R^1$, $R^2$, $R^3$, $R^4$, $R^5$, $R^6$, $R^7$, $R^8$, $R^9$, $R^{10}$, $X^1$ and $X^2$ includes, for example, halogen atoms.

Specific examples of the substituted or unsubstituted $C_{7-20}$ aralkyl include benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (4,6-dimethylphenyl)methyl, (2,3,4-trimethylphenyl)methyl, (2,3,5-trimethylphenyl)methyl, (2,3,6-trimethylphenyl)methyl, (3,4,5-trimethylphenyl)methyl, (2,4,6-trimethylphenyl)methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl)methyl, (sec-butylphenyl)methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n-decylphenyl)methyl, naphthylmethyl and anthracenylmethyl. The preferable example is benzyl. All of these aralkyl groups may be substituted with halogen such as fluorine, chlorine, bromine or iodine.

A substituent for the substituted $C_{6-20}$ aryl denoted by $R^1$, $R^2$, $R^3$, $R^4$, $R^5$, $R^6$, $R^7$, $R^8$, $R^9$, $R^{10}$, $X^1$ and $X^2$ includes, for example, halogen atoms.

Specific examples of the substituted or unsubstituted $C_{6-20}$ aryl include phenyl, 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, n-decylphenyl, n-dodecylphenyl, n-tetradecylphenyl, naphthyl and anthracenyl and the preferable example is phenyl. All of these aryl groups may be substituted with halogen such as fluorine, chlorine, bromine or iodine.

The substituted silyl denoted by $R^1$, $R^2$, $R^3$, $R^4$, $R^5$, $R^6$, $R^7$, $R^8$, $R^9$ and $R^{10}$ is a silyl group substituted with substituted or unsubstituted hydrocarbon. Herein, the hydrocarbon includes $C_{1-10}$ alkyl such as methyl, ethyl, n-propyl, isopropyl, n-butyl, sec-butyl, tert-butyl, isobutyl, n-pentyl, n-hexyl, cyclohexyl, n-heptyl, n-octyl, n-nonyl and n-decyl, and aryl such as phenyl. Specific examples of the substituted silyl having 1 to 20 carbon atoms include mono-substituted silyl having 1 to 20 carbon atoms such as methylsilyl, ethylsilyl and phenylsilyl; di-substituted silyl substituted with $C_{1-20}$ hydrocarbon groups such as dimethylsilyl, diethylsilyl and diphenylsilyl; and tri-substituted silyl substituted with $C_{1-20}$ hydrocarbon groups such as trimethylsilyl, triethylsilyl, tri-n-propylsilyl, triisopropylsilyl, tri-n-butylsilyl, tri-sec-butylsilyl, tri-tert-butylsilyl, tri-isobutylsilyl, tert-butyl-dimethylsilyl, tri-n-pentylsilyl, tri-n-hexylsilyl, tricyclohexylsilyl and triphenylsilyl, and the preferable examples are trimethylsilyl, tert-butyldimethylsilyl and triphenylsilyl. The hydrocarbon groups constituting these substituted silyl groups may be unsubstituted groups as described above, or may be substituted with halogen such as fluorine, chlorine, bromine or iodine.

A substituent for the substituted or unsubstituted $C_{1-20}$ alkoxy denoted by $R^1$, $R^2$, $R^3$, $R^4$, $R^5$, $R^6$, $R^7$, $R^8$, $R^9$, $R^{10}$, $X^1$ and $X^2$ includes, for example, halogen atoms. Specific examples of the substituted or unsubstituted $C_{1-20}$ alkoxy include methoxy, ethoxy, n-propoxy, isopropoxy, n-butoxy, sec-butoxy, tert-butoxy, n-pentyloxy, neopentyloxy, n-hexyloxy, n-octyloxy, n-nonyloxy, n-decyloxy, n-dodecyloxy, n-undecyloxy, n-dodecyloxy, tridecyloxy, tetradecyloxy, n-pentadecyloxy, hexadecyloxy, heptadecyloxy, octadecyloxy, nonadecyloxy and n-eicosyloxy, and the preferable examples are methoxy, ethoxy and tert-butoxy. All of these alkoxy groups may be substituted with halogen such as fluorine, chlorine, bromine or iodine.

A substituent for the substituted or unsubstituted $C_{7-20}$ aralkyloxy denoted by $R^1$, $R^2$, $R^3$, $R^4$, $R^5$, $R^6$, $R^7$, $R^8$, $R^9$, $R^{10}$, $X^1$ and $X^2$ includes, for example, halogen atoms. Specific examples of the substituted or unsubstituted $C_{7-20}$ aralkyloxy include benzyloxy, (2-methylphenyl)methoxy, (3-methylphenyl)methoxy, (4-methylphenyl)methoxy, (2,3-dimethylphenyl)methoxy, (2,4-dimethylphenyl)methoxy, (2,5-dimethylphenyl)methoxy, (2,6-dimethylphenyl)methoxy, (3,4-dimethylphenyl)methoxy, (3,5-dimethylphenyl)methoxy, (2,3,4-trimethylphenyl)methoxy, (2,3,5-trimethylphenyl)methoxy, (2,3,6-trimethylphenyl)methoxy, (2,4,5-trimethylphenyl)methoxy, (2,4,6-trimethylphenyl)methoxy, (3,4,5-trimethylphenyl)methoxy, (2,3,4,5-tetramethylphenyl)methoxy, (2,3,4,6-tetramethylphenyl)methoxy, (2,3,5,6-tetramethylphenyl)methoxy, (pentamethylphenyl)methoxy, (ethylphenyl)methoxy, (n-propylphenyl)methoxy, (isopropylphenyl)methoxy, (n-butylphenyl)methoxy, (sec-butylphenyl)methoxy, (tert-butylphenyl)methoxy, (n-hexylphenyl)methoxy, (n-octylphenyl)methoxy, (n-decylphenyl)methoxy, naphthylmethoxy and anthracenylmethoxy, and the preferable example is benzyloxy. All of these aralkyloxy groups may be substituted with halogen such as fluorine, bromine, chlorine or iodine.

A substituent for the substituted $C_{6-20}$ aryloxy denoted by $R^1$, $R^2$, $R^3$, $R^4$, $R^5$, $R^6$, $R^7$, $R^8$, $R^9$, $R^{10}$, $X^1$ and $X^2$ includes, for example, halogen atoms. Specific examples of the unsubstituted $C_{6-20}$ aryloxy include phenoxy, 2-methylphenoxy, 3-methylphenoxy, 4-methylphenoxy, 2,3-dimethylphenoxy, 2,4-dimethylphenoxy, 2,5-dimethylphenoxy, 2,6-dimethylphenoxy, 3,4-dimethylphenoxy, 3,5-dimethylphenoxy, 2,3,4-trimethylphenoxy, 2,3,5-trimethylphenoxy, 2,3,6-trimethylphenoxy, 2,4,5-trimethylphenoxy, 2,4,6-trimethylphenoxy, 3,4,5-trimethylphenoxy, 2,3,4,5-tetramethylphenoxy, 2,3,4,6-tetramethylphenoxy, 2,3,5,6-tetramethylphenoxy, pentamethylphenoxy, ethylphenoxy, n-propylphenoxy, isoprylphenoxy, n-butylphenoxy, sec-butylphenoxy, tert-butylphenoxy, n-hexylphenoxy, n-octylphenoxy, n-decylphenoxy, n-tetradecylphenoxy, naphthoxy and anthracenoxy. Specific examples of the substituted $C_{6-20}$ aryloxy include, for example, the above unsubstituted $C_{6-20}$ aryloxy which is substituted with halogen such as fluorine, chlorine, bromine or iodine.

The amino substituted with $C_{1-20}$ hydrocarbon denoted by $R^1$, $R^2$, $R^3$, $R^4$, $R^5$, $R^6$, $R^7$, $R^8$, $R^9$, $R^{10}$, $X^1$ and $X^2$ is an amino substituted with two hydrocarbon groups. Herein, the hydrocarbon groups include, for example, $C_{1-20}$ alkyl such as methyl, ethyl, n-propyl, isopropyl, n-butyl, sec-butyl, tert-butyl, isobutyl, n-pentyl, n-hexyl and cyclohexyl, and aryl such as phenyl and these groups may be bonded with one another to form ring(s).

The amino substituted with $C_{1-20}$ hydrocarbon includes, for example, dimethylamino, diethylamino, di-n-propylamino, diisopropylamino, di-n-butylamino, di-sec-butylamino, di-tert-butylamino, diisobutylamino, tert-butylisopropylamino, di-n-hexylamino, di-n-octylamino, di-n-decylamino, diphenylamino, bis(trimethylsilyl)amino, bis(tert-butyldimethylsilyl)amino, pyrrolyl, pyrrolidinyl, piperidinyl, carbozolyl, dihydroindolyl and dihydroisoindolyl, and the preferable examples are dimethylamino, diethylamino, pyrrolydinyl and piperidinyl.

The silyloxy substituted with $C_{1-20}$ hydrocarbon denoted by $R^1$, $R^2$, $R^3$ and $R^4$ is silyloxy substituted with three hydrocarbon groups. Herein, the hydrocarbon groups include, for example, as described above, $C_{1-20}$ alkyl such as methyl, ethyl, n-propyl, isopropyl, n-butyl, sec-butyl, tert-butyl, isobutyl, n-pentyl, n-hexyl and cyclohexyl, and aryl such as phenyl, and these groups may be bonded with one another to form ring(s). The substituted silyloxy having 1 to 20 carbon atoms includes, for example, trimethylsilyloxy, triethylsilyloxy, tri-n-butylsilyloxy, triphenylsilyloxy, triisopropylsilyloxy, tert-butyldimethylsilyloxy, dimethylphenylsilyloxy and methyldiphenylsilyloxy and the preferable examples are trimethylsilyloxy, triphenylsilyloxy and triisopropylsilyloxy.

The phosphino substituted with $C_{1-20}$ hydrocarbon denoted by $R^1$, $R^2$, $R^3$ and $R^4$ is phosphino substituted with two hydrocarbon groups. Herein, the hydrocarbon groups include $C_{1-20}$ alkyl such as methyl, ethyl, n-propyl, isopropyl, n-butyl, sec-butyl, tert-butyl, isobutyl, n-pentyl, n-hexyl, cyclohexyl, heptyl, n-octyl, n-nonyl, n-decyl, n-dodecyl, n-tridecyl, tetradecyl, pentadecyl, hexadecyl, heptadecyl, octadecyl, nonadecyl and n-eicosyl, and aryl such as phenyl, and these groups may be bonded with one another to form ring(s). Specific examples of the phosphino substituted with $C_{1-20}$ hydrocarbon include dimethylphosphino, diethylphosphino, di-n-propylphosphino, diisopropylphosphino, di-n-butylthio, di-sec-butylphosphino, di-tert-butylphosphino, di-isobutylphosphino, tert-butylisopropylphosphino, di-n-hexylphosphino, di-n-octylphosphino, di-n-decylphosphino, diphenylphosphino, bistrimethylsilylphosphino and bis-tert-butyldimethylsilylphosphino and the preferably examples are dimethylphosphino, diethylphosphino and diphenylphosphino.

Hydrocarbon groups for the thio substituted with $C_{1-20}$ hydrocarbon denoted by $R^1$, $R^2$, $R^3$ and $R^4$ include $C_{1-20}$ alkyl such as methyl, ethyl, n-propyl, isopropyl, n-butyl, sec-butyl, tert-butyl, isobutyl, n-pentyl, n-hexyl and cyclohexyl and aryl such as phenyl, and these groups may be bonded with one another to form ring(s) or thiophene. Specific examples of such thio substituted with $C_{1-20}$ hydrocarbon include methylthio, ethylthio, n-propylthio, isopropylthio, n-butylthio, sec-butylthio, tert-butylthio, isobutylthio, n-hexylthio, n-octylthio, n-decylthio and phenylthio.

At least one of $R^1$, $R^2$, $R^3$ and $R^4$ is substituted or unsubstituted $C_{1-20}$ alkoxy, substituted or unsubstituted $C_{6-20}$ aryloxy, substituted or unsubstituted $C_{7-20}$ aralkyloxy, silyloxy substituted with substituted or unsubstituted $C_{1-20}$ hydrocarbon, amino substituted with substituted or unsubstituted $C_{1-20}$ hydrocarbon, phosphino substituted with substituted or unsubstituted $C_{1-20}$ hydrocarbon or thio substituted with substituted or unsubstituted $C_{1-20}$ hydrocarbon.

Two adjacent substituents among $R^1$, $R^2$, $R^3$ and $R^4$, and two adjacent substituents among $R^6$, $R^7$, $R^8$, $R^9$ and $R^{10}$ may be each optionally bonded to form ring(s).

As a ring formed by bond of two adjacent substituents of $R^1$, $R^2$, $R^3$ and $R^4$, for example, saturated or unsaturated hydrocarbon rings and heterocycles such as a furan ring, a thiophene ring and a pyrrole ring can be exemplified.

An example of the transition metal complex represented by the formula (1) in which adjacent $R^3$ and $R^4$ are bonded to form a thiophene ring is, for example, a transition metal complex represented by the following formula (7):

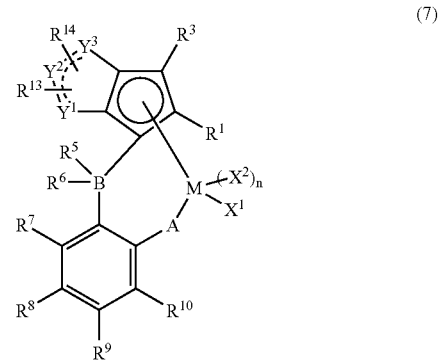

(7)

wherein M, A, B, $R^1$, $R^2$, $R^5$, $R^6$, $R^7$, $R^8$, $R^9$, $R^{10}$, $X^1$, $X^2$ and n are as defined for the formula (1), $R^{13}$ and $R^{14}$ are independently a substituent selected from the group (I) and the bond moiety represented by

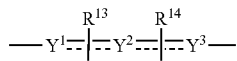

is a partial structure represented by the formula (7a):

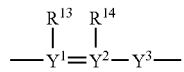 (7a)

wherein $Y^1$ and $Y^2$ are independently a carbon atom and $Y^3$ is a sulfur atom, or by the formula (7b):

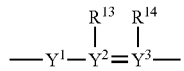 (7b)

wherein $Y^1$ is a sulfur atom and $Y^2$ and $Y^3$ are independently a carbon atom.

An example of the transition metal complex represented by the formula (1) in which adjacent $R^1$ and $R^2$ and adjacent $R^3$ and $R^4$ are each bonded to form a thiophene ring is a transition metal complex represented by the following formula (8):

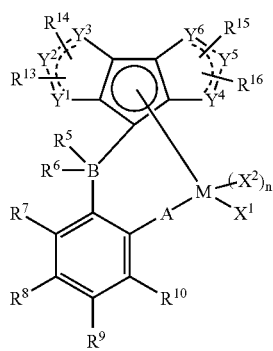 (8)

wherein M, A, B, $R^5$, $R^6$, $R^7$, $R^8$, $R^9$, $R^{10}$, $R^{13}$, $X^1$, $X^2$, $Y^1$, $Y^2$, $Y^3$, $R^{13}$, $R^{14}$, the dotted line and n are as defined for the formulas (1) and (7), $R^{15}$ and $R^{16}$ are independently a substituent selected from the group (I) and the bond moiety represented by

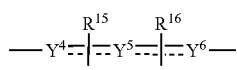

is a partial structure represented by the formula (8a):

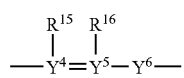 (8a)

wherein $Y^4$ and $Y^5$ are independently a carbon atom and $Y^6$ is a sulfur atom, or by the formula (8b):

 (8b)

wherein $Y^4$ is a sulfur atom and $Y^5$ and $Y^6$ are independently a carbon atom.

As the ring formed by bond of two adjacent substituents among $R^6$, $R^7$, $R^8$, $R^9$ and $R^{10}$, saturated or unsaturated hydrocarbon ring(s) which are substituted with substituted or unsubstituted $C_{1-20}$ hydrocarbon can be exemplified. Specific examples thereof include a cyclopropane ring, a cyclobutane ring, a cyclopentane ring, a cyclohexane ring, a cycloheptane ring, a cyclooctane ring, a benzene ring, a naphthalene ring and an anthracene ring.

Specific examples of the transition metal complex represented by the formula (1) include, for example, dimethylsilyl(3-[pyrrolidin-1-yl]-inden-1-yl)(2-phenoxy)titanium dichloride, dimethylsilyl(3-[pyrrolidin-1-yl]-inden-1-yl)(3-methyl-2-phenoxy)titanium dichloride, dimethylsilyl(3-[pyrrolidin-1-yl]-inden-1-yl)(3,5-dimethyl-2-phenoxy)titanium dichloride, dimethylsilyl(3-[pyrrolidin-1-yl]-inden-1-yl)(3-tert-butyl-2-phenoxy)titanium dichloride, dimethylsilyl(3-[pyrrolidin-1-yl]-inden-1-yl)(3-tert-butyl-5-methyl-2-phenoxy)titanium dichloride, dimethylsilyl(3-[pyrrolidin-1-yl]-inden-1-yl)(3,5-di-tert-butyl-2-phenoxy)titanium dichloride, dimethylsilyl(3-[pyrrolidin-1-yl]-inden-1-yl)(5-methyl-3-phenyl-2-phenoxy)titanium dichloride, dimethylsilyl(3-[pyrrolidin-1-yl]-inden-1-yl)(3-tert-butyldimethylsilyl-5-methyl-2-phenoxy)titanium dichloride, dimethylsilyl(3-[pyrrolidin-1-yl]-inden-1-yl)(5-methyl-3-trimethylsilyl-2-phenoxy)titanium dichloride, dimethylsilyl(3-[pyrrolidin-1-yl]-inden-1-yl)(3-tert-butyl-5-methoxy-2-phenoxy)titanium dichloride, dimethylsilyl(3-[pyrrolidin-1-yl]-inden-1-yl)(3-tert-butyl-5-chloro-2-phenoxy)titanium dichloride, dimethylsilyl(3-[pyrrolidin-1-yl]-inden-1-yl)(3,5-diamyl-2-phenoxy)titanium dichloride, dimethylsilyl(2-[pyrrolidin-1-yl]-inden-1-yl)(2-phenoxy)titanium dichloride, dimethylsilyl(2-[pyrrolidin-1-yl]-inden-1-yl)(3-methyl-2-phenoxy)titanium dichloride, dimethylsilyl(2-[pyrrolidin-1-yl]-inden-1-yl)(3,5-dimethyl-2-phenoxy)titanium dichloride, dimethylsilyl(2-[pyrrolidin-1-yl]-inden-1-yl)(3-tert-butyl-2-phenoxy)titanium dichloride, dimethylsilyl(2-[pyrrolidin-1-yl]-inden-1-yl)(3-tert-butyl-5-methyl-2-phenoxy)titanium dichloride, dimethylsilyl(2-[pyrrolidin-1-yl]-inden-1-yl)(3,5-di-tert-butyl-2-phenoxy)titanium dichloride, dimethylsilyl(2-[pyrrolidin-1-yl]-inden-1-yl)(5-methyl-3-phenyl-2-phenoxy)titanium dichloride, dimethylsilyl(2-[pyrrolidin-1-yl]-inden-1-yl)(3-tert-butyldimethylsilyl-5-methyl-2-phenoxy)titanium dichloride, dimethylsilyl(2-[pyrrolidin-1-yl]-inden-1-yl)(5-methyl-3-trimethylsilyl-2-phenoxy)titanium dichloride, dimethylsilyl(2-[pyrrolidin-1-yl]-inden-1-yl)(3-tert-butyl-5-methoxy-2-phenoxy)titanium dichloride, dimethylsilyl(2-[pyrrolidin-1-yl]-inden-1-yl)(3-tert-butyl-5-chloro-2-phenoxy)titanium dichloride, dimethylsilyl(2-[pyrrolidin-1-yl]-inden-1-yl)(3,5-diamyl-2-phenoxy)titanium dichloride, dimethylsilyl(3-[piperidin-1-yl]-inden-1-yl)(2-phenoxy)titanium dichloride, dimethylsilyl(3-[piperidin-1-yl]-inden-1-yl)(3-methyl-2-phenoxy)titanium dichloride, dimethylsilyl(3-[piperidin-1-yl]-inden-1-yl)(3,5-dimethyl-2-phenoxy)titanium dichloride, dimethylsilyl(3-[piperidin-1-yl]-inden-1-yl)(3-tert-butyl-2-phenoxy)titanium dichloride, dimethylsilyl(3-

[piperidin-1-yl]-inden-1-yl)(3-tert-butyl-5-methyl-2-phenoxy)titanium dichloride, dimethylsilyl(3-[piperidin-1-yl]-inden-1-yl)(3,5-di-tert-butyl-2-phenoxy)titanium dichloride, dimethylsilyl(3-[piperidin-1-yl]-inden-1-yl)(5-methyl-3-phenyl-2-phenoxy)titanium dichloride, dimethylsilyl(3-[piperidin-1-yl]-inden-1-yl)(3-tert-butyldimethylsilyl-5-methyl-2-phenoxy)titanium dichloride, dimethylsilyl(3-[piperidin-1-yl]-inden-1-yl)(5-methyl-3-trimethylsilyl-2-phenoxy)titanium dichloride, dimethylsilyl(3-[piperidin-1-yl]-inden-1-yl)(3-tert-butyl-5-methoxy-2-phenoxy)titanium dichloride, dimethylsilyl(3-[piperidin-1-yl]-inden-1-yl)(3-tert-butyl-5-chloro-2-phenoxy)titanium dichloride, dimethylsilyl(3-[piperidin-1-yl]-inden-1-yl)(3,5-diamyl-2-phenoxy)titanium dichloride, dimethylsilyl(2-dimethylaminoinden-1-yl)(2-phenoxy)titanium dichloride, dimethylsilyl(2-dimethylaminoinden-1-yl)(3-methyl-2-phenoxy)titanium dichloride, dimethylsilyl(2-dimethylaminoinden-1-yl)(3,5-dimethyl-2-phenoxy)titanium dichloride, dimethylsilyl(2-dimethylaminoinden-1-yl)(3-tert-butyl-2-phenoxy)titanium dichloride, dimethylsilyl(2-dimethylaminoinden-1-yl)(3-tert-butyl-5-methyl-2-phenoxy)titanium dichloride, dimethylsilyl(2-dimethylaminoinden-1-yl)(3,5-di-tert-butyl-2-phenoxy)titanium dichloride, dimethylsilyl(2-dimethylaminoinden-1-yl)(5-methyl-3-phenyl-2-phenoxy)titanium dichloride, dimethylsilyl(2-dimethylaminoinden-1-yl)(3-tert-butyldimethylsilyl-5-methyl-2-phenoxy)titanium dichloride, dimethylsilyl(2-dimethylaminoinden-1-yl)(5-methyl-3-trimethylsilyl-2-phenoxy)titanium dichloride, dimethylsilyl(2-dimethylaminoinden-1-yl)(3-tert-butyl-5-methoxy-2-phenoxy)titanium dichloride, dimethylsilyl(2-dimethylaminoinden-1-yl)(3-tert-butyl-5-chloro-2-phenoxy)titanium dichloride, dimethylsilyl(2-dimethylaminoinden-1-yl)(3,5-diamyl-2-phenoxy)titanium dichloride, dimethylsilyl(4,5-dimethyl-2-dimethylaminocyclopentadienyl)(2-phenoxy)titanium dichloride, dimethylsilyl(4,5-dimethyl-2-dimethylaminocyclopentadienyl)(3-methyl-2-phenoxy)titanium dichloride, dimethylsilyl(4,5-dimethyl-2-dimethylaminocyclopentadienyl)(3,5-dimethyl-2-phenoxy)titanium dichloride, dimethylsilyl(4,5-dimethyl-2-dimethylaminocyclopentadienyl)(3-tert-butyl-2-phenoxy)titanium dichloride, dimethylsilyl(4,5-dimethyl-2-dimethylaminocyclopentadienyl)(3-tert-butyl-5-methyl-2-phenoxy)titanium dichloride, dimethylsilyl(4,5-dimethyl-2-dimethylaminocyclopentadienyl)(3,5-di-tert-butyl-2-phenoxy)titanium dichloride, dimethylsilyl(4,5-dimethyl-2-dimethylaminocyclopentadienyl)(5-methyl-3-phenyl-2-phenoxy)titanium dichloride, dimethylsilyl(4,5-dimethyl-2-dimethylaminocyclopentadienyl)(3-tert-butyldimethylsilyl-5-methyl-2-phenoxy)titanium dichloride, dimethylsilyl(4,5-dimethyl-2-dimethylaminocyclopentadienyl)(5-methyl-3-trimethylsilyl-2-phenoxy)titanium dichloride, dimethylsilyl(4,5-dimethyl-2-dimethylaminocyclopentadienyl)(3-tert-butyl-5-methoxy-2-phenoxy)titanium dichloride, dimethylsilyl(4,5-dimethyl-2-dimethylaminocyclopentadienyl)(3-tert-butyl-5-chloro-2-phenoxy)titanium dichloride, dimethylsilyl(4,5-dimethyl-2-dimethylaminocyclopentadienyl)(3,5-diamyl-2-phenoxy)titanium dichloride, dimethylsilyl(3-[pyrrolidin-1-yl]-2-methylinden-1-yl)(2-phenoxy)titanium dichloride, dimethylsilyl(3-[pyrrolidin-1-yl]-2-methylinden-1-yl)(3-methyl-2-phenoxy)titanium dichloride, dimethylsilyl(3-[pyrrolidin-1-yl]-2-methylinden-1-yl)(3,5-dimethyl-2-phenoxy)titanium dichloride, dimethylsilyl(3-[pyrrolidin-1-yl]-2-methylinden-1-yl)(3-tert-butyl-2-phenoxy)titanium dichloride, dimethylsilyl(3-[pyrrolidin-1-yl]-2-methylinden-1-yl)(3-tert-butyl-5-methyl-2-phenoxy)titanium dichloride, dimethylsilyl(3-[pyrrolidin-1-yl]-2-methylinden-1-yl)(3,5-di-tert-butyl-2-phenoxy)titanium dichloride, dimethylsilyl(3-[pyrrolidin-1-yl]-2-methylinden-1-yl)(5-methyl-3-phenyl-2-phenoxy)titanium dichloride, dimethylsilyl(3-[pyrrolidin-1-yl]-2-methylinden-1-yl)(3-tert-butyldimethylsilyl-5-methyl-2-phenoxy)titanium dichloride, dimethylsilyl(3-[pyrrolidin-1-yl]-2-methylinden-1-yl)(5-methyl-3-trimethylsilyl-2-phenoxy)titanium dichloride, dimethylsilyl(3-[pyrrolidin-1-yl]-2-methylinden-1-yl)(3-tert-butyl-5-methoxy-2-phenoxy)titanium dichloride, dimethylsilyl(3-[pyrrolidin-1-yl]-2-methylinden-1-yl)(3-tert-butyl-5-chloro-2-phenoxy)titanium dichloride, dimethylsilyl(3-[pyrrolidin-1-yl]-2-methylinden-1-yl)(3,5-diamyl-2-phenoxy)titanium dichloride, dimethylsilyl(2-methoxyinden-1-yl)(2-phenoxy)titanium dichloride, dimethylsilyl(2-methoxyinden-1-yl)(3-methyl-2-phenoxy)titanium dichloride, dimethylsilyl(2-methoxyinden-1-yl)(3,5-dimethyl-2-phenoxy)titanium dichloride, dimethylsilyl(2-methoxyinden-1-yl)(3-tert-butyl-2-phenoxy)titanium dichloride, dimethylsilyl(2-methoxyinden-1-yl)(3-tert-butyl-5-methyl-2-phenoxy)titanium dichloride, dimethylsilyl(2-methoxyinden-1-yl)(3,5-di-tert-butyl-2-phenoxy)titanium dichloride, dimethylsilyl(2-methoxyinden-1-yl)(5-methyl-3-phenyl-2-phenoxy)titanium dichloride, dimethylsilyl(2-methoxyinden-1-yl)(3-tert-butyldimethylsilyl-5-methyl-2-phenoxy)titanium dichloride, dimethylsilyl(2-methoxyinden-1-yl)(5-methyl-3-trimethylsilyl-2-phenoxy)titanium dichloride, dimethylsilyl(2-methoxyinden-1-yl)(3-tert-butyl-5-methoxy-2-phenoxy)titanium dichloride, dimethylsilyl(2-methoxyinden-1-yl)(3-tert-butyl-5-chloro-2-phenoxy)titanium dichloride, dimethylsilyl(2-methoxyinden-1-yl)(3,5-diamyl-2-phenoxy)titanium dichloride, dimethylsilyl(3-[dihydroisoindolin-2-yl]-inden-1-yl)(2-phenoxy)titanium dichloride, dimethylsilyl(3-[dihydroisoindolin-2-yl]-inden-1-yl)(3-methyl-2-phenoxy)titanium dichloride, dimethylsilyl(3-[dihydroisoindolin-2-yl]-inden-1-yl)(3,5-dimethyl-2-phenoxy)titanium dichloride, dimethylsilyl(3-[dihydroisoindolin-2-yl]-inden-1-yl)(3-tert-butyl-2-phenoxy)titanium dichloride, dimethylsilyl(3-[dihydroisoindolin-2-yl]-inden-1-yl)(3-tert-butyl-5-methyl-2-phenoxy)titanium dichloride, dimethylsilyl(3-[dihydroisoindolin-2-yl]-inden-1-yl)(3,5-di-tert-butyl-2-phenoxy)titanium dichloride, dimethylsilyl(3-[dihydroisoindolin-2-yl]-inden-1-yl)(5-methyl-3-phenyl-2-phenoxy)titanium dichloride, dimethylsilyl(3-[dihydroisoindolin-2-yl]-inden-1-yl)(3-tert-butyldimethylsilyl-5-methyl-2-phenoxy)titanium dichloride, dimethylsilyl(3-[dihydroisoindolin-2-yl]-inden-1-yl)(5-methyl-3-trimethylsilyl-2-phenoxy)titanium dichloride, dimethylsilyl(3-[dihydroisoindolin-2-yl]-inden-1-yl)(3-tert-butyl-5-methoxy-2-phenoxy)titanium dichloride, dimethylsilyl(3-[dihydroisoindolin-2-yl]-inden-1-yl)(3-tert-butyl-5-chloro-2-phenoxy)titanium dichloride, dimethylsilyl(3-[dihydroisoindolin-2-yl]-inden-1-yl)(3,5-diamyl-2-phenoxy)titanium dichloride, dimethylsilyl(3-diphenylphosphinoinden-1-yl)(2-phenoxy)titanium dichloride, dimethylsilyl(3-diphenylphosphinoinden-1-yl)(3-methyl-2-phenoxy)titanium dichloride, dimethylsilyl(3-diphenylphosphinoinden-1-yl)(3,5-dimethyl-2-phenoxy)titanium dichloride, dimethylsilyl(3-diphenylphosphinoinden-1-yl)(3-tert-butyl-2-phenoxy)titanium dichloride, dimethylsilyl(3-diphenylphosphinoinden-1-yl)(3-tert-butyl-5-methyl-2-phenoxy)titanium dichloride, dimethylsilyl(3-diphenylphosphinoinden-1-yl)(3,5-di-tert-butyl-2-phenoxy)titanium dichloride, dimethylsilyl(3-diphenylphosphinoinden-1-yl)(5-methyl-3-phenyl-2-phenoxy)titanium dichloride, dimethylsilyl(3- diphenylphosphinoinden-1-yl)(3-tert-butyldimethylsilyl-5-methyl-2-phenoxy)titanium dichloride, dimethylsilyl(3-diphenylphosphinoinden-1-yl)(5-methyl-3-trimethylsilyl-2-phenoxy)titanium dichloride, dimethylsilyl(3-diphenylphosphinoinden-1-yl)(3-tert-butyl-5-methoxy-2-phenoxy)titanium dichloride, dimethylsilyl(3-diphenylphosphinoinden-1-yl)(3-tert-butyl-5-chloro-2-phenoxy)titanium dichloride, dimethylsilyl(3-diphenylphosphinoinden-1-yl)(3,5-diamyl-2-phenoxy)titanium dichloride, dimethylsilyl(2,4,5-trimethyl-cyclopenta[2,3-b]thiophen-6-yl)(2-phenoxy)titanium dichloride, dimethylsilyl(2,4,5-trimethyl-cyclopenta[2,3-b]thiophen-6-yl)(3-methyl-2-phenoxy)titanium dichloride, dimethylsilyl(2,4,5-trimethyl-cyclopenta[2,3-b]thiophen-6-yl)(3,5-dimethyl-2-phenoxy)titanium dichloride, dimethylsilyl(2,4,5-trimethyl-cyclopenta[2,3-b]thiophen-6-yl)(3-tert-butyl-2-phenoxy)titanium dichloride, dimethylsilyl(2,4,5-trimethyl-cyclopenta[2,3-b]thiophen-6-yl)(3-tert-butyl-5-methyl-2-phenoxy)titanium dichloride, dimethylsilyl(2,4,5-trimethyl-cyclopenta[2,3-b]thiophen-6-yl)(3,5-di-tert-butyl-2-phenoxy)titanium dichloride, dimethylsilyl(2,4,5-trimethyl-cyclopenta[2,3-b]thiophen-6-yl)(5-methyl-3-phenyl-2-phenoxy)titanium dichloride, dimethylsilyl(2,4,5-trimethyl-cyclopenta[2,3-b]thiophen-6-yl)(3-tert-butyldimethylsilyl-5-methyl-2-phenoxy)titanium dichloride, dimethylsilyl(2,4,5-trimethyl-cyclopenta[2,3-b]thiophen-6-yl)(5-methyl-3-trimethylsilyl-2-phenoxy)titanium dichloride, dimethylsilyl(2,4,5-trimethyl-cyclopenta[2,3-b]thiophen-6-yl)(3-tert-butyl-5-methoxy-2-phenoxy)titanium dichloride, dimethylsilyl(2,4,5-trimethyl-cyclopenta[2,3-b]thiophen-6-yl)(3-tert-butyl-5-chloro-2-phenoxy)titanium dichloride, dimethylsilyl(2,4,5-trimethyl-cyclopenta[2,3-b]thiophen-6-yl)(3,5-diamyl-2-phenoxy)titanium dichloride, dimethylsilyl(2,5-dimethylcyclopenta[1,2-b:4,3-b']dithiophen-7-yl)(2-phenoxy)titanium dichloride, dimethylsilyl(2,5-dimethylcyclopenta[1,2-b:4,3-b']dithiophen-7-yl)(3-methyl-2-phenoxy)titanium dichloride, dimethylsilyl(2,5-dimethylcyclopenta[1,2-b:4,3-b']dithiophen-7-yl)(3,5-dimethyl-2-phenoxy)titanium dichloride, dimethylsilyl(2,5-dimethylcyclopenta[1,2-b:4,3-b']dithiophen-7-yl)(3-tert-butyl-2-phenoxy)titanium dichloride, dimethylsilyl(2,5-dimethylcyclopenta[1,2-b:4,3-b']dithiophen-7-yl)(3-tert-butyl-5-methyl-2-phenoxy)titanium dichloride, dimethylsilyl(2,5-dimethylcyclopenta[1,2-b:4,3-b']dithiophen-7-yl)(3,5-di-tert-butyl-2-phenoxy)titanium dichloride, dimethylsilyl(2,5-dimethylcyclopenta[1,2-b:4,3-b']dithiophen-7-yl)(5-methyl-3-phenyl-2-phenoxy)titanium dichloride, dimethylsilyl(2,5-dimethylcyclopenta[1,2-b:4,3-b']dithiophen-7-yl)(3-tert-butyldimethylsilyl-5-methyl-2-phenoxy)titanium dichloride, dimethylsilyl(2,5-dimethylcyclopenta[1,2-b:4,3-b']dithiophen-7-yl)(5-methyl-3-trimethylsilyl-2-phenoxy)titanium dichloride, dimethylsilyl(2,5-dimethylcyclopenta[1,2-b:4,3-b']dithiophen-7-yl)(3-tert-butyl-5-methoxy-2-phenoxy)titanium dichloride, dimethylsilyl(2,5-dimethylcyclopenta[1,2-b:4,3-b']dithiophen-7-yl)(3-tert-butyl-5-chloro-2-phenoxy)titanium dichloride, dimethylsilyl(2,5-dimethylcyclopenta[1,2-b:4,3-b']dithiophen-7-yl)(3,5-diamyl-2-phenoxy)titanium dichloride, dimethylsilyl(5-methyl-1-phenyl-cyclopenta[3,2-b]pyrrol-4-yl)(2-phenoxy)titanium dichloride, dimethylsilyl(5-methyl-1-phenyl-cyclopenta[3,2-b]pyrrol-4-yl)(3-methyl-2-phenoxy)titanium dichloride, dimethylsilyl(5-methyl-1-phenyl-cyclopenta[3,2-b]pyrrol-4-yl)(3,5-dimethyl-2-phenoxy)titanium dichloride, dimethylsilyl(5-methyl-1-phenyl-cyclopenta[3,2-b]pyrrol-4-yl)(3-tert-butyl-2-phenoxy)titanium dichloride, dimethylsilyl(5-methyl-1-phenyl-cyclopenta[3,2-b]pyrrol-4-yl)(3-tert-butyl-5-methyl-2-phenoxy)titanium dichloride, dimethylsilyl(5-methyl-1-phenyl-cyclopenta[3,2-b]pyrrol-4-yl)(3,5-di-tert-butyl-2-phenoxy)titanium dichloride, dimethylsilyl(5-methyl-1-phenyl-cyclopenta[3,2-b]pyrrol-4-yl)(5-methyl-3-phenyl-2-phenoxy)titanium dichloride, dimethylsilyl(5-methyl-1-phenyl-cyclopenta[3,2-b]pyrrol-4-yl)(3-tert-butyldimethylsilyl-5-methyl-2-phenoxy)titanium dichloride, dimethylsilyl(5-methyl-1-phenyl-cyclopenta[3,2-b]pyrrol-4-yl)(5-methyl-3-trimethylsilyl-2-phenoxy)titanium dichloride, dimethylsilyl(5-methyl-1-phenyl-cyclopenta[3,2-b]pyrrol-4-yl)(3-tert-butyl-5-methoxy-2-phenoxy)titanium dichloride, dimethylsilyl(5-methyl-1-phenyl-cyclopenta[3,2-b]pyrrol-4-yl)(3-tert-butyl-5-chloro-2-phenoxy)titanium dichloride, and dimethylsilyl(5-methyl-1-phenyl-cyclopenta[3,2-b]pyrrol-4-yl)(3,5-diamyl-2-phenoxy)titanium dichloride; compounds obtained by replacing 2-phenoxy of the above mentioned compounds with 3-phenyl-2-phenoxy, 3-trimethylsilyl-2-phenoxy or 3-tert-butyldimethylsilyl-2-phenoxy; compounds obtained by replacing dimethylsilyl of the above mentioned compounds with diethylsilyl, diphenylsilyl or dimethoxysilyl; compounds obtained by replacing titanium of the above mentioned compounds with zirconium or hafnium; compounds obtained replacing chloride of the above mentioned compounds with bromide, iodide, dimethylamide, diethylamide, methoxide, n-butoxide, isopropoxide, methyl or benzyl; and transition metal complexes represented by the formula (1) in which B is a Group 14 element in the periodic table other than silicon.

Such a transition metal complex (1) may be produced by, for example, reacting the substituted cyclopenadiene represented by the formula (2) with a base and then with a transition metal compound represented by the formula (3).

Of the substituted or unsubstituted hydrocarbon group denoted by $R^{11}$ the unsubstituted hydrocarbon group includes $C_{1-10}$ alkyl such as methyl, ethyl, propyl, butyl, pentyl, hexyl, heptyl, octyl, nonyl and decyl; $C_{2-10}$ alkenyl such as vinyl, allyl, propenyl, 2-methyl-2-propenyl, homoallyl, pentenyl, hexenyl, heptenyl, octenyl, nonenyl and decenyl; and $C_{7-12}$ aralkyl such as benzyl, (4-methylphenyl)methyl and (2,4,6-trimethylphenyl)methyl. The substituted hydrocarbon group includes alkoxyalkyl such as methoxymethyl or methoxyethoxymethyl and further, halogen-substituted hydrocarbon groups, which hydrocarbon groups are the above mentioned unsubstituted hydrocarbon groups, whose example is 2-chloro-2-propenyl.

The tri-substituted silyl group includes trimethylsilyl, triethylsilyl, tri-n-propylsilyl, triisopropylsilyl, tri-n-butylsilyl, tri-sec-butylsilyl, tri-tert-butylsilyl, tri-isobutylsilyl, tert-butyl-dimethylsilyl, tri-n-pentylsilyl, tri-n-hexylsilyl, tricyclohexylsilyl and triphenylsilyl. Among such substituents denoted by $R^{11}$, alkenyl, particularly allyl is preferred in terms of high yield in production of the transition metal complex represented by the formula (1)

The hydrogen, halogen, substituted or unsubstituted $C_{1-20}$ alkyl, substituted or unsubstituted $C_{7-20}$ aralkyl, substituted or unsubstituted $C_{6-20}$ aryl, silyl substituted with substituted or unsubstituted $C_{1-20}$ hydrocarbon, substituted or unsubstituted $C_{1-20}$ alkoxy, substituted or unsubstituted $C_{1-20}$ aralkyloxy, substituted or unsubstituted $C_{1-20}$ aryloxy and di-substituted amino having 2 to 20 carbon atoms denoted by $X^3$ or $X^4$ include those exemplified as $X^1$ and $X^2$ in the transition metal complex represented by the formula (1).

The base that may be used for production of the compound represented by the formula (1) includes organic alkali metal compounds, for example, organolithium compounds such as methyl lithium, ethyl lithium, n-butyl lithium, sec-butyl lithium, tert-butyl lithium, lithium trimethylsilylacetylide, lithium acetylide, trimethylsilylmethyl lithium, vinyl lithium, phenyl lithium and allyl lithium. The used amount of the base is generally in a range of 0.5 to 5 moles per 1 mole of the compound (2).

Further, the base may be used in combination with an amine compound. Such an amine compound includes primary amine compounds such as methylamine, ethylamine, n-propylamine, isopropylamine, n-butylamine, tert-butylamine, n-octylamine, n-decylamine, aniline and ethylenediamine, secondary amine compounds such as dimethylamine, diethylamine, di-n-propylamine, di-n-butylamine, di-tert-butylamine, di-n-octylamine, di-n-decylamine, pyrrolidine, hexamethyldisilazane and diphenylamine, and tertiary amine compounds such as trimethylamine, triethylamine, tri-n-propylamine, tri-n-butylamine, diisopropylethylamine, tri-n-octylamine, tri-n-decylamine, triphenylamine, N,N-dimethylaniline, N,N,N',N'-tetramethylethylenediamine, N-methylpyrrolidine and 4-dimethylaminopyridine. The used amount of such an amine compound is generally in a range of 10 moles or less, preferably 0.5 to 10 moles, more preferably 1 to 3 moles per 1 mole of the base.

The reaction is generally carried out in an inert solvent. Such a solvent includes aprotic solvents, for example, aromatic hydrocarbon solvents such as benzene or toluene, aliphatic hydrocarbon solvents such as hexane or heptane, ether solvents such as diethyl ether, tetrahydrofuran or 1,4-dioxane, amide solvents such as hexamethylphosphoric amide or dimethylformamide, polar solvents such as acetonitrile, propionitrile, acetone, diethyl ketone, methyl isobutyl ketone and cyclohexanone, and halogenated solvents such as dichloromethane, dichloroethane, chlorobenzene or dichlorobenzene. These solvents may be used alone or as a mixture of two or more of them and the used amount is generally in range of 1 to 200 parts by weight, preferably 3 to 50 parts by weight per 1 part by weight of substituted cyclopentadiene represented by the formula (2).

This reaction may be generally carried out by adding substituted cyclopentadiene represented by the formula (2) and the base to the solvent and then adding the transition metal compound represented by the formula (3). A solid that may be precipitated after adding substituted cyclopentadiene represented by the formula (2) and the base to the solvent may be removed from the reaction system and then added to the same solvent as described above and then the transition metal compound represented by the formula (3) may be added thereto. Alternatively, substituted cyclopentadiene represented by the formula (2), the base and the transition metal compound represented by the formula (3) may be added simultaneously. The reaction temperature is generally $-100°$ C. or higher to the boiling point of the solvent or lower, preferably in a range of $-80$ to $100°$ C. It is preferable that the reaction system is shielded from light in terms of the yield of the transition metal complex represented by the formula (1).

From the reaction mixture thus obtained, the aimed transition metal complex represented by the formula (1) can be obtained by a conventional method, for example, by filtrating off a produced precipitate, concentrating the filtrate to produce a transition metal complex represented by the formula (1), and then separating it by filtration.

The substituted cyclopentadiene represented by the formula (2) is produced, for example, by reacting substituted cyclopentadiene represented by the formula (5):

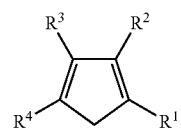

wherein $R^1$, $R^2$, $R^3$ and $R^4$ are as defined above, with a base and then reacting with a compound represented by the formula (6):

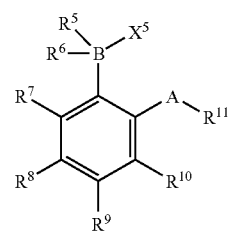

wherein $X^5$ is halogen, and A, B, $R^5$, $R^6$, $R^7$, $R^8$, $R^9$, $R^{10}$ and $R^{11}$ are as defined above.

This step is generally carried out by adding the compound (5) and a base to a solvent and then adding the compound (6) thereto. The reaction temperature is generally in a range from $-100°$ C. to the boiling point of a solvent. In the case that an organic alkali metal compound is used as the base, it is preferably in a range of $-80$ to $40°$ C.

Such a base is not particularly limited and includes organic alkali metal compounds, for example, organolithium compounds such as methyl lithium, ethyl lithium, n-butyl lithium, sec-butyl lithium, tert-butyl lithium, lithium trimethylsilylacetylide, lithium acetylide, trimethylsilylmethyl lithium, vinyl lithium, phenyl lithium and allyl lithium, and inorganic bases such as sodium hydride, potassium hydride, sodium methoxide and potassium butoxide. The used amount of the base is generally in a range of 0.5 to 5 moles per 1 mole of the compound (2).

The reaction mixture containing the compound (2) thus obtained may be used as it is in a solution form in the next step or after adding water or an aqueous acidic solution to the mixture, separating the organic layer, drying it and then removing the solvent by distillation. Preferably, after the reaction mixture thus obtained is distilled under reduced pressure to remove the solvent, a hydrocarbon solvent is added to the residue, insoluble substances are filtered off and the resulting filtrate is concentrated under reduced pressure to obtain a residue, which is used in the next step. The compound (2) thus obtained may be further purified by recrystallization, distillation, column chromatography, or the like.

Specific examples of the substituted cyclopentadiene represented by the formula (2) include, for example, (2-allyloxyphenyl)(3-[pyrrolidin-1-yl]-1H-inden-1-yl)dimethylsilane, (2-allyloxy-3-methylphenyl)(3-[pyrrolidin-1-yl]-1H-inden-1-yl)dimethylsilane, (2-allyloxy-3,5-dimethylphenyl)(3-[pyrrolidin-1-yl]-1H-inden-1-yl)dimethylsilane, (2-allyloxy-3-tert-butylphenyl)(3-[pyrrolidin-1-yl]-1H-inden-1-yl)dimethylsilane, (2-allyloxy-3-tert-butyl-5-methylphenyl)(3-[pyrrolidin-1-yl]-1H-inden-1-yl)dimethylsilane, (2-allyloxy-3,5-di-tert-butylphenyl)(3-[pyrrolidin-1- yl]-1H-inden-1-yl)dimethylsilane, (2-allyloxy-5-methyl-3-phenylphenyl)(3-[pyrrolidin-1-yl]-1H-inden-1-yl)dimethylsilane, (2-allyloxy-5-methyl-3-trimethylsilylphenyl)(3-[pyrrolidin-1-yl]-1H-inden-1-yl)dimethylsilane, (2-allyloxy-3-tert-butyldimethylsilyl-5-methylphenyl)(3-[pyrrolidin-1-yl]-1H-inden-1-yl)dimethylsilane, (2-allyloxy-3,5-diamylphenyl)(3-[pyrrolidin-1-yl]-1H-inden-1-yl)dimethylsilane, (2-allyloxy-3-tert-butyl-5-methoxyphenyl)(3-[pyrrolidin-1-yl]-1H-inden-1-yl)dimethylsilane, (6-allyloxy-5-tert-butyl-3-chlorophenyl)(3-[pyrrolidin-1-yl]-1H-inden-1-yl)dimethylsilane, (2-allyloxyphenyl)(2-[pyrrolidin-1-yl]-1H-inden-1-yl)dimethylsilane, (2-allyloxy-3-methylphenyl)(2-[pyrrolidin-1-yl]]-1H-inden-1-yl)dimethylsilane, (2-allyloxy-3,5-dimethylphenyl)(2-[pyrrolidin-1-yl]]-1H-inden-1-yl)dimethylsilane, (2-allyloxy-3-tert-butylphenyl)(2-[pyrrolidin-1-yl]]-1H-inden-1-yl)dimethylsilane, (2-allyloxy-3-tert-butyl-5-methylphenyl)(2-[pyrrolidin-1-yl]]-1H-inden-1-yl)dimethylsilane, (2-allyloxy-3,5-di-tert-butylphenyl)(2-[pyrrolidin-1-yl]]-1H-inden-1-yl)dimethylsilane, (2-allyloxy-5-methyl-3-phenylphenyl)(2-[pyrrolidin-1-yl]]-1H-inden-1-yl)dimethylsilane, (2-allyloxy-5-methyl-3-trimethylsilylphenyl)(2-[pyrrolidin-1-yl]]-1H-inden-1-yl)dimethylsilane, (2-allyloxy-3-tert-butyldimethylsilyl-5-methylphenyl)(2-[pyrrolidin-1-yl]]-1H-inden-1-yl)dimethylsilane, (2-allyloxy-3,5-diamylphenyl)(2-[pyrrolidin-1-yl]]-1H-inden-1-yl)dimethylsilane, (2-allyloxy-3-tert-butyl-5-methoxyphenyl)(2-[pyrrolidin-1-yl]-1H-inden-1-yl)dimethylsilane, (6-allyloxy-5-tert-butyl-3-chlorophenyl)(2-[pyrrolidin-1-yl]]-1H-inden-1-yl)dimethylsilane, (2-allyloxyphenyl)(3-[piperidin-1-yl]-1H-inden-1-yl)dimethylsilane, (2-allyloxy-3-methylphenyl)(3-[piperidin-1-yl]-1H-inden-1-yl)dimethylsilane, (2-allyloxy-3,5-dimethylphenyl)(3-[piperidin-1-yl]-1H-inden-1-yl)dimethylsilane, (2-allyloxy-3-tert-butylphenyl)(3-[piperidin-1-yl]-1H-inden-1-yl)dimethylsilane, (2-allyloxy-3-tert-butyl-5-methylphenyl)(3-[piperidin-1-yl]-1H-inden-1-yl)dimethylsilane, (2-allyloxy-3,5-di-tert-butylphenyl)(3-[piperidin-1-yl]-1H-inden-1-yl)dimethylsilane, (2-allyloxy-5-methyl-3-phenylphenyl)(3-[piperidin-1-yl]-1H-inden-1-yl)dimethylsilane, (2-allyloxy-5-methyl-3-trimethylsilylphenyl)(3-[piperidin-1-yl]-1H-inden-1-yl)dimethylsilane, (2-allyloxy-3-tert-butyldimethylsilyl-5-methylphenyl)(3-[piperidin-1-yl]-1H-inden-1-yl)dimethylsilane, (2-allyloxy-3,5-diamylphenyl)(3-[piperidin-1-yl]-1H-inden-1-yl)dimethylsilane, (2-allyloxy-3-tert-butyl-5-methoxyphenyl)(3-[piperidin-1-yl]-1H-inden-1-yl)dimethylsilane, (6-allyloxy-5-tert-butyl-3-chlorophenyl)(3-[piperidin-1-yl]-1H-inden-1-yl)dimethylsilane, (2-allyloxyphenyl)(2-dimethyl-1H-inden-1-yl)dimethylsilane, (2-allyloxy-3-methylphenyl)(2-dimethylamino-1H-inden-1-yl)dimethylsilane, (2-allyloxy-3,5-dimethylphenyl)(2-dimethylamino-1H-inden-1-yl)dimethylsilane, (2-allyloxy-3-tert-butylphenyl)(2-dimethylamino-1H-inden-1-yl)dimethylsilane, (2-allyloxy-3-tert-butyl-5-methylphenyl)(2-dimethylamino-1H-inden-1-yl)dimethylsilane, (2-allyloxy-3,5-di-tert-butylphenyl)(2-dimethylamino-1H-inden-1-yl)dimethylsilane, (2-allyloxy-5-methyl-3-phenylphenyl)(2-dimethylamino-1H-inden-1-yl)dimethylsilane, (2-allyloxy-5-methyl-3-trimethylsilylphenyl)(2-dimethylamino-1H-inden-1-yl)dimethylsilane, (2-allyloxy-3-tert-butyldimethylsilyl-5-methylphenyl)(2-dimethylamino-1H-inden-1-yl)dimethylsilane, (2-allyloxy-3,5-diamylphenyl)(2-dimethylamino-1H-inden-1-yl)dimethylsilane, (2-allyloxy-3-tert-butyl-5-methoxyphenyl)(2-dimethylamino-1H-inden-1-yl)dimethylsilane, (6-allyloxy-5-tert-butyl-3-chlorophenyl)(2-dimethylamino-1H-inden-1-yl)dimethylsilane, (2-allyloxyphenyl)(4,5-dimethyl-2-dimethylaminocyclopentadienyl)dimethylsilane, (2-allyloxy-3-methylphenyl)(4,5-dimethyl-2-dimethylaminocyclopentadienyl)dimethylsilane, (2-allyloxy-3,5-dimethylphenyl)(4,5-dimethyl-2-dimethylaminocyclopentadienyl)dimethylsilane, (2-allyloxy-3-tert-butylphenyl)(4,5-dimethyl-2-dimethylaminocyclopentadienyl)dimethylsilane, (2-allyloxy-3-tert-butyl-5-methylphenyl)(4,5-dimethyl-2-dimethylaminocyclopentadienyl)dimethylsilane, (2-allyloxy-3,5-di-tert-butylphenyl)(4,5-dimethyl-2-dimethylaminocyclopentadienyl)dimethylsilane, (2-allyloxy-5-methyl-3-phenylphenyl)(4,5-dimethyl-2-dimethylaminocyclopentadienyl)dimethylsilane, (2-allyloxy-5-methyl-3-trimethylsilylphenyl)(4,5-dimethyl-2-dimethylaminocyclopentadienyl)dimethylsilane, (2-allyloxy-3-tert-butyldimethylsilyl-5-methylphenyl)(4,5-dimethyl-2-dimethylaminocyclopentadienyl)dimethylsilane, (2-allyloxy-3,5-diamylphenyl)(4,5-dimethyl-2-dimethylaminocyclopentadienyl)dimethylsilane, (2-allyloxy-3-tert-butyl-5-methoxyphenyl)(4,5-dimethyl-2-dimethylaminocyclopentadienyl)dimethylsilane, (6-allyloxy-5-tert-butyl-3-chlorophenyl)(4,5-dimethyl-2-dimethylaminocyclopentadienyl)dimethylsilane, (2-allyloxyphenyl)(3-[pyrrolidin-1-yl]-2-methyl-1H-inden-1-yl)dimethylsilane, (2-allyloxy-3-methylphenyl)(3-[pyrrolidin-1-yl]-2-methyl-1H-inden-1-yl)dimethylsilane, (2-allyloxy-3,5-dimethylphenyl)(3-[pyrrolidin-1-yl]-2-methyl-1H-inden-1-yl)dimethylsilane, (2-allyloxy-3-tert-butylphenyl)(3-[pyrrolidin-1-yl]-2-methyl-1H-inden-1-yl)dimethylsilane, (2-allyloxy-3-tert-butyl-5-methylphenyl)(3-[pyrrolidin-1-yl]-2-methyl-1H-inden-1-yl)dimethylsilane, (2-allyloxy-3,5-di-tert-butylphenyl)(3-[pyrrolidin-1-yl]-2-methyl-1H-inden-1-yl)dimethylsilane, (2-allyloxy-5-methyl-3-phenylphenyl)(3-[pyrrolidin-1-yl]-2-methyl-1H-inden-1-yl)dimethylsilane, (2-allyloxy-5-methyl-3-trimethylsilylphenyl)(3-[pyrrolidin-1-yl]-2-methyl-1H-inden-1-yl)dimethylsilane, (2-allyloxy-3-tert-butyldimethylsilyl-5-methylphenyl)(3-[pyrrolidin-1-yl]-2-methyl-1H-inden-1-yl)dimethylsilane, (2-allyloxy-3,5-diamylphenyl)(3-[pyrrolidin-1-yl]-2-methyl-1H-inden-1-yl)dimethylsilane, (2-allyloxy-3-tert-butyl-5-methoxyphenyl)(3-[pyrrolidin-1-yl]-2-methyl-1H-inden-1-yl)dimethylsilane, (6-allyloxy-5-tert-butyl-3-chlorophenyl)(3-[pyrrolidin-1-yl]-2-methyl-1H-inden-1-yl)dimethylsilane, (2-allyloxyphenyl)(2-methoxyl-1H-inden-1-yl)dimethylsilane, (2-allyloxy-3-methylphenyl)(2-methoxyl-1H-inden-1-yl)dimethylsilane, (2-allyloxy-3,5-dimethylphenyl)(2-methoxyl-1H-inden-1-yl)dimethylsilane, (2-allyloxy-3-tert-butylphenyl)(2-methoxyl-1H-inden-1-yl)dimethylsilane, (2-allyloxy-3-tert-butyl-5-methylphenyl)(2-methoxyl-1H-inden-1-yl)dimethylsilane, (2-allyloxy-3,5-di-tert-butylphenyl)(2-methoxyl-1H-inden-1-yl)dimethylsilane, (2-allyloxy-5-methyl-3-phenylphenyl)(2-methoxyl-1H-inden-1-yl)dimethylsilane, (2-allyloxy-5-methyl-3-trimethylsilylphenyl)(2-methoxyl-1H-inden-1-yl)dimethylsilane, (2-allyloxy-3-tert-butyldimethylsilyl-5-methylphenyl)(2-methoxyl-1H-inden-1-yl)dimethylsilane, (2-allyloxy-3,5-diamylphenyl)(2-methoxyl-1H-inden-1-yl)dimethylsilane, (2-allyloxy-3-tert-butyl-5-methoxyphenyl)(2-methoxyl-1H-inden-1-yl)dimethylsilane, (6-allyloxy-5-tert-butyl-3-chlorophenyl)(2-methoxyl-1H-inden-1-yl)dimethylsilane, (2-allyloxyphenyl)(3-[dihydroisoindolin-2-yl]-1H-inden-1-yl)dimethylsilane, (2-allyloxy-3-methylphenyl)(3-[dihydroisoindolin-2-yl]-1H-inden-1-yl)dimethylsilane, (2-allyloxy-3,5-dimethylphenyl)(3-[dihydroisoindolin-2-yl]-1H-inden-1-yl)dimethylsilane, (2-allyloxy-3-tert-butylphenyl)(3-[dihydroisoindolin-2-yl]-1H-inden-1-yl)dimethylsilane, (2-allyloxy-3-tert-butyl-5-methylphenyl)(3-[dihydroisoindolin-2-yl]-1H-inden-1-yl)dimethylsilane, (2-allyloxy-3,5-di-tert-butylphenyl)(3-[dihydroisoindolin-2-yl]-1H-inden-1-yl)dimethylsilane, (2-allyloxy-5-methyl-3-phenylphenyl)(3-[dihydroisoindolin-2-yl]-1H-inden-1-yl)dimethylsilane, (2-allyloxy-5-methyl-3-trimethylsilylphenyl)(3-[dihydroisoindolin-2-yl]-1H-inden-1-yl)dimethylsilane, (2-allyloxy-3-tert-butyldimethylsilyl-5-methylphenyl)(3-[dihydroisoindolin-2-yl]-1H-inden-1-yl)dimethylsilane, (2-allyloxy-3,5-diamylphenyl)(3-[dihydroisoindolin-2-yl]-1H-inden-1-yl)dimethylsilane, (2-allyloxy-3-tert-butyl-5-methoxyphenyl)(3-[dihydroisoindolin-2-yl]-1H-inden-1-yl)dimethylsilane, (6-allyloxy-5-tert-butyl-3-chlorophenyl)(3-[dihydroisoindolin-2-yl]-1H-inden-1-yl)dimethylsilane, (1-allyloxynaphthalen-2-yl)(3-[dihydroisoindolin-2-yl]-1H-inden-1-yl)dimethylsilane, (2-allyloxyphenyl)(3-diphenylphosphino-1H-inden-1-yl)dimethylsilane, (2-allyloxy-3-methylphenyl)(3-diphenylphosphino-1H-inden-1-yl)dimethylsilane, (2-allyloxy-3,5-dimethylphenyl)(3-diphenylphosphino-1H-inden-1-yl)dimethylsilane, (2-allyloxy-3-tert-butylphenyl)(3-diphenylphosphino-1H-inden-1-yl)dimethylsilane, (2-allyloxy-3-tert-butyl-5-methylphenyl)(3-diphenylphosphino-1H-inden-1-yl)dimethylsilane, (2-allyloxy-3,5-di-tert-butylphenyl)(3-diphenylphosphino-1H-inden-1-yl)dimethylsilane, (2-allyloxy-5-methyl-3-phenylphenyl)(3-diphenylphosphino-1H-inden-1-yl)dimethylsilane, (2-allyloxy-5-methyl-3-trimethylsilylphenyl)(3-diphenylphosphino-1H-inden-1-yl)dimethylsilane, (2-allyloxy-3-tert-butyldimethylsilyl-5-methylphenyl)(3-diphenylphosphino-1H-inden-1-yl)dimethylsilane, (2-allyloxy-3,5-diamylphenyl)(3-diphenylphosphino-1H-inden-1-yl)dimethylsilane, (2-allyloxy-3-tert-butyl-5-methoxyphenyl)(3-diphenylphosphino-1H-inden-1-yl)dimethylsilane, (6-allyloxy-5-tert-butyl-3-chlorophenyl)(3-diphenylphosphino-1H-inden-1-yl)dimethylsilane, (1-allyloxynaphthalen-2-yl)(3-diphenylphosphino-1H-inden-1-yl)dimethylsilane, (2-allyloxyphenyl)(2,4,5-trimethyl-6-hydrocyclopenta[2,3-b]thiophen-6-yl)dimethylsilane, (2-allyloxy-3-methylphenyl)(2,4,5-trimethyl-6-hydrocyclopenta[2,3-b]thiophen-6-yl)dimethylsilane, (2-allyloxy-3,5-dimethylphenyl)(2,4,5-trimethyl-6-hydrocyclopenta[2,3-b]thiophen-6-yl)dimethylsilane, (2-allyloxy-3-tert-butylphenyl)(2,4,5-trimethyl-6-hydrocyclopenta[2,3-b]thiophen-6-yl)dimethylsilane, (2-allyloxy-3-tert-butyl-5-methylphenyl)(2,4,5-trimethyl-6-hydrocyclopenta[2,3-b]thiophen-6-yl)dimethylsilane, (2-allyloxy-3,5-di-tert-butylphenyl)(2,4,5-trimethyl-6-hydrocyclopenta[2,3-b]thiophen-6-yl)dimethylsilane, (2-allyloxy-5-methyl-3-phenylphenyl)(2,4,5-trimethyl-6-hydrocyclopenta[2,3-b]thiophen-6-yl)dimethylsilane, (2-allyloxy-5-methyl-3-trimethylsilylphenyl)(2,4,5-trimethyl-6-hydrocyclopenta[2,3-b]thiophen-6-yl)dimethylsilane, (2-allyloxy-3-tert-butyldimethylsilyl-5-methylphenyl)(2,4,5-trimethyl-6-hydrocyclopenta[2,3-b]thiophen-6-yl)dimethylsilane, (2-allyloxy-3,5-diamylphenyl)(2,4,5-trimethyl-6-hydrocyclopenta[2,3-b]thiophen-6-yl)dimethylsilane, (2-allyloxy-3-tert-butyl-5-methoxyphenyl)(2,4,5-trimethyl-6-hydrocyclopenta[2,3-b]thiophen-6-yl)dimethylsilane, (6-allyloxy-5-tert-butyl-3-chlorophenyl)(2,4,5-trimethyl-6-hydrocyclopenta[2,3-b]thiophen-6-yl)dimethylsilane, (1-allyloxynaphthalen-2-yl)(2,4,5-trimethyl-6-hydrocyclopenta[2,3-b]thiophen-6-yl)dimethylsilane, (2-allyloxyphenyl)(2,5-dimethyl-6-hydrocyclopenta[2,3-b]thiophen-6-yl)dimethylsilane, (2-allyloxy-3-methylphenyl)(2,5-dimethyl-6-hydrocyclopenta[2,3-b]thiophen-6-yl)dimethylsilane, (2-allyloxy-3,5-dimethylphenyl)(2,5-dimethyl-6-hydrocyclopenta[2,3-b]thiophen-6-yl)dimethylsilane, (2-allyloxy-3-tert-butylphenyl)(2,5-dimethyl-6-hydrocyclopenta[2,3-b]thiophen-6-yl)dimethylsilane, (2-allyloxy-3-tert-butyl-5-methylphenyl)(2,5-dimethyl-6-hydrocyclopenta[2,3-b]thiophen-6-yl)dimethylsilane, (2-allyloxy-3,5-di-tert-butylphenyl)(2,5-dimethyl-6-hydrocyclopenta[2,3-b]thiophen-6-yl)dimethylsilane, (2-allyloxy-5-methyl-3-phenylphenyl)(2,5-dimethyl-6-hydrocyclopenta[2,3-b]thiophen-6-yl)dimethylsilane, (2-allyloxy-5-methyl-3-trimethylsilylphenyl)(2,5-dimethyl-6-hydrocyclopenta[2,3-b]thiophen-6-yl)dimethylsilane, (2-allyloxy-3-tert-butyldimethylsilyl-5-methylphenyl)(2,5-dimethyl-6-hydrocyclopenta[2,3-b]thiophen-6-yl)dimethylsilane, (2-allyloxy-3,5-diamylphenyl)(2,5-dimethyl-6-hydrocyclopenta[2,3-b]thiophen-6-yl)dimethylsilane, (2-allyloxy-3-tert-butyl-5-methoxyphenyl)(2,5-dimethyl-6-hydrocyclopenta[2,3-b]thiophen-6-yl)dimethylsilane, (6-allyloxy-5-tert-butyl-3-chlorophenyl)(2,5-dimethyl-6-hydrocyclopenta[2,3-b]thiophen-6-yl)dimethylsilane, (1-allyloxynaphthalen-2-yl)(2,5-dimethyl-6-hydrocyclopenta[2,3-b]thiophen-6-yl)dimethylsilane, (2-allyloxyphenyl)(2,5-dimethylcyclopenta[1,2-b:4,3-b']dithiophen-7-yl)dimethylsilane, (2-allyloxy-3-methylphenyl)(2,5-dimethylcyclopenta[1,2-b:4,3-b']dithiophen-7-yl)dimethylsilane, (2-allyloxy-3,5-dimethylphenyl)(2,5-dimethylcyclopenta[1,2-b:4,3-b']dithiophen-7-yl)dimethylsilane, (2-allyloxy-3-tert-butylphenyl)(2,5-dimethylcyclopenta[1,2-b:4,3-b']dithiophen-7-yl)dimethylsilane, (2-allyloxy-3-tert-butyl-5-methylphenyl)(2,5-dimethylcyclopenta[1,2-b:4,3-b']dithiophen-7-yl)dimethylsilane, (2-allyloxy-3,5-di-tert-butylphenyl)(2,5-dimethylcyclopenta[1,2-b:4,3-b']dithiophen-7-yl)dimethylsilane, (2-allyloxy-5-methyl-3-phenylphenyl)(2,5-dimethylcyclopenta[1,2-b:4,3-b']dithiophen-7-yl)dimethylsilane, (2-allyloxy-5-methyl-3-trimethylsilylphenyl)(2,5-dimethylcyclopenta[1,2-b:4,3-b']dithiophen-7-yl)dimethylsilane, (2-allyloxy-3-tert-butyldimethylsilyl-5-methylphenyl)(2,5-dimethylcyclopenta[1,2-b:4,3-b']dithiophen-7-yl)dimethylsilane, (2-allyloxy-3,5-diamylphenyl)(2,5-dimethylcyclopenta[1,2-b:4,3-b']dithiophen-7-yl)dimethylsilane, (2-allyloxy-3-tert-butyl-5-methoxyphenyl)(2,5-dimethylcyclopenta[1,2-b:4,3-b']dithiophen-7-yl)dimethylsilane, (6-allyloxy-5-tert-butyl-3-chlorophenyl)(2,5-dimethylcyclopenta[1,2-b:4,3-b']dithiophen-7-yl)dimethylsilane, (1-allyloxynaphthalen-2-yl)(2,5-dimethylcyclopenta[1,2-b:4,3-b']dithiophen-7-yl)dimethylsilane, (2-allyloxyphenyl)(5-methyl-1-phenyl-4-hydrocyclopenta[3,2-b]pyrrol-4-yl)dimethylsilane, (2-allyloxy-3-methylphenyl)(5-methyl-1-phenyl-4-hydrocyclopenta[3,2-b]pyrrol-4-yl)dimethylsilane, (2-allyloxy-3,5-dimethylphenyl)(5-methyl-1-phenyl-4-hydrocyclopenta[3,2-b]pyrrol-4-yl)dimethylsilane, (2-allyloxy-3-tert-butylphenyl)(5-methyl-1-phenyl-4-hydrocyclopenta[3,2-b]pyrrol-4-yl)dimethylsilane, (2-allyloxy-3-tert-butyl-5-methylphenyl)(5-methyl-1-phenyl-4-hydrocyclopenta[3,2-b]pyrrol-4-yl)dimethylsilane, (2-allyloxy-3,5-di-tert-butylphenyl)(5-methyl-1-phenyl-4-hydrocyclopenta[3,2-b]pyrrol-4-yl)dimethylsilane, (2-allyloxy-5-methyl-3-phenylphenyl)(5-methyl-1-phenyl-4-hydrocyclopenta[3,2-b]pyrrol-4-yl)dimethylsilane, (2-allyloxy-5-methyl-3-trimethylsilylphenyl)(5-methyl-1-phenyl-4-hydrocyclopenta[3,2-b]pyrrol-4-yl)dimethylsilane, (2-allyloxy-3-tert-butyldimethylsilyl-5-methylphenyl)(5-methyl-1-phenyl-4-hydrocyclopenta[3,2-b]pyrrol-4-yl)dimethylsilane, (2-allyloxy-3,5-diamylphenyl)(5-methyl-1-phenyl-4-hydrocyclopenta[3,2-b]pyrrol-4-yl)dimethylsilane, (2-allyloxy-3-tert-butyl-5-methoxyphenyl)(5-methyl-1-phenyl-4-hydrocyclopenta[3,2-b]pyrrol-4-yl)dimethylsilane, (6-allyloxy-5-tert-butyl-3-chlorophenyl)(5-methyl-1-phenyl-4-hydrocyclopenta[3,2-b]pyrrol-4-yl)dimethylsilane, and (1-allyloxynaphthalen-2-yl)(5-methyl-1-phenyl-4-hydrocyclopenta[3,2-b]pyrrol-4-yl)dimethylsilane; compounds obtained by replacing allyloxy of the above mentioned compounds with methoxy, benzyloxy, ethoxy, trimethylsilyloxy, tert-butyldimethylsilyloxy or methoxymethoxy; compounds obtained by replacing dimethysilane of the above mentioned compounds with diethylsilane, diphenylsilane or dimethoxysilane; compounds obtained by replacing 2-allyloxyphenyl of the above mentioned compounds with 3-phenyl-2-allyloxyphenyl, 3-trimethylsilyl-2-allyloxyphenyl or 3-tert-butyldimethylsilyl-2-allyloxyphenyl; and cyclopentadienyl compounds represented by the formula (2) in which B is a Group 14 element in the periodic table other than silicon.

The transition metal compound represented by the formula (3) includes, for example, titanium halides such as titanium tetrachloride, titanium trichloride, titanium tetrabromide, or titanium tetraiodide, amidotitnaium such as tetrakis(dimethylamino)titanium, dichlorobis(dimethylamino)titanium, trichloro(dimethylamino)titanium or tetrakis (diethylamino)titanium, and alkoxytitanium such as tetraisopropoxytitanium, tetra-n-butoxytitanium, dichlorodiisopropoxytitnaium and trichloroisopropoxytitanium and compuonds obtained by replacing titanium of the above mentioned compounds with zirconium or hafnium, and the preferable example is titanium tetrachloride. The used amount of the transition metal compound represented by the formula (3) is generally in a range of 0.5 to 3 moles, preferably 0.7 to 1.5 moles per 1 mole of substituted cyclopentadiene represented by the formula (2).

The substituted cyclopentadiene represented by the formula (4) may be produced, for example, by reacting 2,5-dimethyl-5,6-dihydrocyclopenta[1,2-b]thiophen-4-one with an alkyl metal or an aryl metal compound to obtain alcohol and then dehydrating said alcohol. According to a procedure similar to a well-known synthesis method of pyrrole analogous compounds (J. Am. Chem. Soc., 2001, vol. 123, p. 4763), 2,5-dimethyl-5,6-dihydrocyclopenta[1,2-b]thiophen-4-one can be produced from 5-methyl-2-thiophenecarboxamide.

For the substituted cyclopentadiene represented by the formula (5), for example, WO 01/47939 discloses a synthesis method of cyclopentadiene compounds substituted with sulfur and WO 01/53360 and WO 00/66596 disclose synthesis methods of cyclopentadiene compounds substituted with nitrogen. Further, WO 01/53361 discloses cyclopentadiene compounds substituted with silicon.

For use in polymerization reaction, the transition metal complex represented by the formula (1) thus produced and the compound (A) or said transition metal complex, the compound (A) and the compound (B) may be added in optional order to a reaction system. Alternatively, said transition metal complex and the compound (A) or said transition metal complex, the compound (A) and the compound (B) may be contacted previously and the resulting reaction mixture may be used in polymerization reaction.

[Compound (A)]

As the compound (A) that may be employed in the present invention, for example, a well-known organoaluminum compound can be used. As the compound (A), a well-known organoaluminum compound is preferably used and more preferred example is any one of or a mixture of two or three of the following compounds (A1) to (A3).

(A1): an organoaluminum compound represented by the formula $E1_aAl(Z)_{(3-a)}$;
(A2): cyclic aluminoxane having the structure represented by the formula $\{-Al(E2)-O-\}_b$;
(A3): linear aluminoxane having the structure represented by the formula $E3\{-Al(E3)-O-\}_cAl(E3)_2$;

wherein E1 to E3 are the same or different and each independently denotes $C_{1-8}$ hydrocarbon, Z is the same or different and denotes hydrogen or halogen, a denotes 1, 2, or 3, b denotes an integer of 2 or more, and c denotes an integer of 1 or more.

Specific examples of the organoaluminum compound (A1) represented by the formula $E1aAl(Z)_{(3-a)}$ include, for example, trialkylaluminum such as trimethylaluminum, triethylaluminum, tripropylaluminum, triisobutylaluminum or trihexylaluminum; dialkylaluminum chloride such as dimethylaluminum chloride, diethylaluminum chloride, dipropylaluminum chloride, diisobutylaluminum chloride or dihexylaluminum chloride; alkylaluminum dichloride such as methylaluminum dichloride, ethylaluminum dichloride, propylaluminum dichloride, isobutylaluminum dichloride or hexylaluminum dichloride; dialkylaluminum hydride such as dimethylaluminum hydride, diethylaluminum hydride, dipropylaluminum hydride, diisobutylaluminum hydride or dihexylaluminum hydride. The preferable example is trialkylaluminum and the more preferable examples are triethylaluminum and triisobutylaluminum.

In the cyclic aluminoxane (A2) represented by the formula $\{-Al(E2)-O-\}_b$ and the linear aluminoxane (A3) represented by the formula $E3\{-Al(E3)-O-\}_cAl(E3)_2$, specific examples of E2 and E3 are alkyl groups such as methyl, ethyl, n-propyl, isopropyl, n-butyl, isobutyl, n-pentyl and neopentyl, b denotes an integer of 2 or more and c denotes an integer of 1 or more. Preferably, E2 and E3 are methyl or isobutyl, b is an integer of 2 to 40 and c is an integer of 1 to 40.

The above-mentioned aluminoxane is produced by a variety of methods. Such methods are not particularly limited and the aluminoxane may be produced in a similar manner to a known method in the art. For example, the aluminoxane is produced by dissolving trialkylaluminum (e.g. trimethylaluminum) in a suitable organic solvent (e.g. benzene, an aliphatic hydrocarbon, and the like) and then contacting said solution with water. In addition, a production process thereof by bringing trialkylaluminum (e.g. trimethylaluminum) into contact with a metal salt containing crystal water (e.g. copper sulfate hydrate) is also exemplified.

[Compound (B)]

As the compound (B) that may be employed in the present invention, any one of or a mixture of two or three of (B1) the boron compound represented by the formula BQ1Q2Q3, (B2) the boron compound represented by the formula $Z^+(BQ1Q2Q3Q4)^-$ or (B3) the boron compound represented by the formula $(L-H)^+(BQ1Q2Q3Q4)^-$ can be exemplified.

In (B1) the boron compound represented by the formula BQ1Q2Q3, B is boron in trivalent valence state and Q1 to Q3 independently denote a halogen atom, a $C_{1-20}$ hydrocarbon group, a halogenated $C_{1-20}$ hydrocarbon group, a substituted silyl group having 1 to 20 carbon atoms, a $C_{1-20}$ alkoxy group or a di-substituted amino group having 2 to 20 carbon atoms, which may be the same or different from one another. Preferable examples of Q1 to Q3 are a halogen atom, a $C_{1-20}$ hydrocarbon group and a halogenated $C_{1-20}$ hydrocarbon group.

Specific examples of (B1) include tris(pentafluorophenyl)borane, tris(2,3,5,6-tetrafluorophenyl)borane, tris(2,3,4,5-tetrafluorophenyl)borane, tris(3,4,5-trifluorophenyl)borane, tris(2,3,4-trifluorophenyl)borane and phenylbis(pentafluorophenyl)borane, and the preferable example is tris(pentafluorophenyl)borane.

In (B2) the boron compound represented by the formula $Z^+(BQ1Q2Q3Q4)^-$, $Z^+$ denotes an inorganic or organic cation, B is boron in trivalent valence state, and Q1 to Q4 are the same as those denoted by Q1 to Q3 in the above-mentioned (B1).

In specific examples of the compound represented by the formula $Z^+(BQ1Q2Q3Q4)^-$, the inorganic cation $Z^+$ includes a ferrocenium cation, an alkyl-substituted ferrocenium cation and a silver cation; the organic cation $Z^+$ includes a triphenylmethyl cation; and $(BQ1Q2Q3Q4)^-$ includes tetrakis(pentafluorophenyl)borate, tetrakis(2,3,5,6-tetrafluorophenyl)borate, tetrakis(2,3,4,5-tetrafluorophenyl)borate, tetrakis(3,4,5-trifluorophenyl)borate, tetrakis(2,2,4-trifluorophenyl)borate, phenylbis(pentafluorophenyl)borate and tetrakis(3,5-bistrifluoromethylphenyl)borate.

Specific combinations of them include ferrocenium tetrakis(pentafluorophenyl)borate, 1,1'-dimethylferrocenium tetrakis(pentafluorophenyl)borate, silver tetrakis(pentafluorophenyl)borate, triphenylmethyl tetrakis(pentafluorophenyl)borate and triphenylmethyl tetrakis(3,5-bistrifluoromethylphenyl)borate, and the preferred example is triphenylmethyl tetrakis(pentafluorophenyl)borate.

In (B3) the boron compound represented by the formula $(L-H)^+(BQ1Q2Q3Q4)^-$, L is a neutral Lewis base, $(L-H)^+$ is a Brønsted acid, B is boron in trivalent valence state and Q1 to Q4 are the same as those denoted by Q1 to Q3 in the above-mentioned formula (B1).

In specific examples of the compound represented by the formula $(L-H)^+(BQ1Q2Q3Q4)^-$, a Brønsted acid denoted by $(L-H)^+$ includes trialkyl-substituted ammonium, N,N-dialkylanilinium, dialkylammonium and triarylphosphonium and examples of $(BQ1Q2Q3Q4)^-$ are as defined above.

Specific combinations of them include triethylammonium tetrakis(pentafluorophenyl)borate, tripropylammonium tetrakis(pentafluorophenyl)borate, tri(n-butyl)ammonium tetrakis(pentafluorophenyl)borate, tri(n-butyl)ammonium tetrakis(3,5-bistrifluoromethylphenyl)borate, N,N-dimethylanilinium tetrakis(pentafluorophenyl)borate, N,N-diethylanilinium tetrakis(pentafluorophenyl)borate, N,N-2,4,6-pentamethylanilinium tetrakis(pentafluorophenyl)borate, N,N-dimethylanilinium tetrakis(3,5-bistrifluoromethylphenyl)borate, diisopropylammonium tetrakis(pentafluorophenyl)borate, dicyclohexylammonium tetrakis(pentafluorophenyl)borate, triphenylphosphonium tetrakis(pentafluorophenyl)borate, tri(methylphenyl)phosphonium tetrakis(pentafluorophenyl)borate and tri(dimethylphenyl)phosphonium tetrakis(pentafluorophenyl)borate and the preferred examples are tri(n-butyl)ammonium tetrakis(pentafluorophenyl)borate and N,N-dimethylanilinium tetrakis(pentafluorophenyl)borate.

With respect to the amount of each catalytic component that may be used, it is desirable to use each catalytic component so that the molar ratio of the compound (A)/the transition metal complex (1) is in a range of 0.1 to 10,000, preferably 5 to 2,000 and the molar ratio of the compound (B)/the transition metal complex (1) is in a range of 0.01 to 100, preferably 0.5 to 10.

With respect to the concentration of each catalytic component in the case of using it in a solution form, it is desirable that the transition metal complex represented by the formula (1) is used in a range of 0.0001 to 5 mmol/L, preferably 0.001 to 1 mmol/L; the compounds (A) is used in a range of 0.01 to 500 mmol/L, preferably 0.1 to 100 mmol/L on the basis of Al atom; and the compounds (B) is used in a range of 0.0001 to 5 mmol/L, preferably 0.001 to 1 mmol/L.

Monomers employed for polymerization in the present invention may be olefin or diolefin having 2 to 20 carbon atoms and two or more kinds of monomers may be used simultaneously. The following are examples of such monomers, but the present invention is not limited to these exemplified compounds. Specific examples of such olefin include, for example, ethylene, propylene, butene-1, pentene-1, hexene-1, heptene-1, octene-1, nonene-1, decene-1, 5-methyl-2-pentene-1, vinylcyclohexene, 2-norbornene, cyclohexene and dicyclopentadiene. Diolefin compounds may be conjugated diene or non-conjugated diene of hydrocarbon compounds and specific examples thereof include the non-conjugated diene compounds such as 1,5-hexadiene, 1,4-hexadiene, 1,4-pentadiene, 1,7-octadiene, 1,8-nonadiene, 1,9-decadiene, 4-methyl-1,4-hexadiene, 5-methyl-1,4-hexadiene, 7-methyl-1,6-octadiene, 5-ethylidene-2-norbornene, dicyclopentadiene, 5-vinyl-2-norbornene, 5-methyl-2-norbornene, norbornadiene, 5-methylene-2-norbornene, 1,5-cyclooctadiene or 5,8-endomethylenehexahydronaphthalene, and the conjugated diene compounds such as 1,3-butadiene, isoprene, 1,3-hexadiene, 1,3-octadiene, 1,3-cyclooctadiene or 1,3-cyclohexadiene. Specific examples of monomers constituting a copolymer include ethylene and propylene; ethylene and butene-1; ethylene and hexene-1; propylene and butene-1; and combinations of the above mentioned combinations and 5-ethylidien-2-norbornene, but the present invention is not limited to the above-mentioned compounds.

In the present invention, aromatic vinyl compounds may be also used as a monomer. Specific examples of the aromatic vinyl compounds include styrene, o-methylstyrene, m-methylstyrene, p-methylstyrene, o,p-dimethylstyrene, o-ethylstyrene, m-ethylstyrene, p-ethylstyrene, o-chlorostyrene, p-chlorostyrene, α-methylstyrene and divinylbenzene.

A method for polymerization is not specifically limited, and for example, may be solvent polymerization or slurry polymerization, in which aliphatic hydrocarbon such as butane, pentane, hexane, heptane or octane, aromatic hydrocarbon such as benzene or toluene, or halogenated hydrocarbon such as methylene dichloride is used as a solvent, or gas phase polymerization in a gaseous monomer, which may be either successive polymerization or batch polymerization.

The polymerization temperature is generally in a range of −50° C. to 250° C. and in order to produce polymers with high molecular weights, it is particularly preferable in a range of −20° C. to 100° C. The polymerization pressure is preferably from the normal pressure (e.g. about 0.1 MPa) to 10 MPa (100 kg/cm$^2$ G). From an industrial viewpoint, high temperature and high pressure polymerization at 100° C. or higher and 10 MPa or higher is sometimes preferable, and such high temperature and high pressure polymerization may be applicable to the present invention. In general, the polymerization time is appropriately determined depending on the types of the aimed polymers and reaction apparatus and it may be generally in a range of 1 minute to 20 hours. In the present invention, a chain transfer agent such as hydrogen may be added to control the molecular weight of a copolymer.

EXAMPLES

The following Examples will illustrate the present invention in details, but they are not intended to limit the present invention.

The following abbreviations are used in Tables 1 to 6.

TIBA: triisobutylaluminum
MMAO: Modified methyl aluminoxane (methylaluminoxane modified by addition of triisobutylaluminum)
AB: dimethylanilinium tetrakis(pentafluorophenyl)borate
CB: triphenylmethyl tetrakis(pentafluorophenyl)borate
PE: polyethylene
Tm: the melting point of a polymer
Mw: the molecular weight of a polymer
Mw/Mn: the molecular weight distribution of a polymer
SCB: the number of methyl branches per 1,000 carbon atoms of a polymer

Example 1

Synthesis of (2-allyloxy-3-tert-butyl-5-methylphenyl)(3-[pyrrolidin-1-yl]-1H-inden-1-yl)dimethylsilane

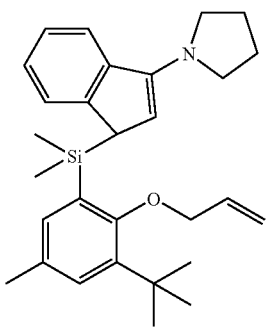

A solution of (2-allyloxy-3-tert-butyl-5-methylphenyl)chlorodimethylsilane (0.82 g, 2.49 mmol) in toluene (4.1 mL) was added dropwise to a solution of 3-(3-[pyrrolidin-1-yl]-1H-inden-1-yl)lithium (0.50 g, 2.62 mmol) tetrahydrofuran (5.6 mL) at 0° C. The resulting reaction mixture was warmed to room temperature and stirred for 18 hours. After the solvent was distilled off under reduced pressure, hexane (20.0 mL) was added and the mixture was filtered to remove insoluble substances. The filtrate was distilled under reduced pressure to quantitatively obtain (2-allyloxy-3-tert-butyl-5-methylphenyl)(3-[pyrrolidin-1-yl]-1H-inden-1-yl)dimethylsilane.

$^1$H-NMR (deuterated benzene, δ(ppm)): 0.15–0.20(6H), 1.41(9H), 1.46–1.50(4H), 2.10(3H), 3.09–3.14(4H), 3.93 (1H), 4.30(2H), 4.99–5.03(1H), 5.43(1H), 5.42–5.48(1H), 5.68–5.82(1H), 7.06–7.60(6H)

Mass spectra (EI, m/z): 445(M$^+$), 261, 233, 210, 184, 115, 73, 57

Example 2

Synthesis of dimethylsilyl(3-[pyrrolidin-1-yl]-inden-1-yl)(3-tert-butyl-5-methyl-2-phenoxy)titanium dichloride [Complex 1]

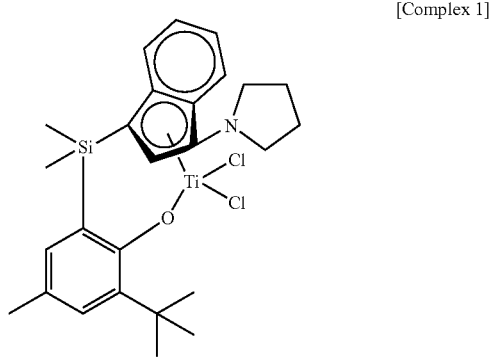

[Complex 1]

A 1.56 M solution of n-butyllithium in hexane (3.74 mL, 2.41 mmol) was added dropwise to a solution of (2-allyloxy-3-tert-butyl-5-methylphenyl)(3-[pyrrolidin-1-yl]-1H-inden-1-yl)dimethylsilane (0.74 g, 1.66 mmol) and triethylamine (1.05 g, 7.47 mmol) in toluene (7.4 mL) at −78° C. and stirred for 10 minutes and then at room temperature for 1 hour. A solution of titanium tetrachloride (0.47 g, 2.49 mmol) in toluene (3.0 mL) was added dropwise to the reaction mixture at −78° C. and the resulting reaction mixture was warmed to 90° C. and then stirred for 3 hours. After insoluble substances were removed by filtration and the solvent was distilled off, the residue was washed with hexane (1.3 mL) to obtain dimethylsilyl(3-[pyrrolidin-1-yl]-inden-1-yl)(3-tert-butyl-5-methyl-2-phenoxy)titanium dichloride (0.66 g, 75.9%) as a brown solid.

$^1$H-NMR (deuterated benzene, δ(ppm)): 0.59(3H), 0.63 (3H), 1.38–1.41(4H), 1.53(9H), 2.29(3H), 3.30–3.40(4H), 5.48(1H), 6.97–7.77(6H)

Mass spectra (FD, m/z): 521 (M$^+$), 454, 403, 296, 295, 185, 184

Example 3

Synthesis of (2-allyloxy-3-tert-butyl-5-methylphenyl)(2,4,5-trimethyl-6-hydrocyclopenta[2,3-b]thiophen-6-yl)dimethylsilane

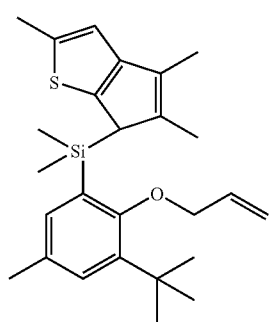

A solution of (2-allyloxy-3-tert-buyl-5-methylphenyl)chlorodimethylsilane (0.83 g, 2.80 mmol) in toluene (2 mL) was added dropwise to a solution of (2,4,5-trimethyl-6-hydrocyclopenta[2,3-b]thiophen-6-yl)lithium (0.50 g, 2.94 mmol) in tetrahydrofuran (20 mL) at −78° C. The resulting reaction mixture was warmed to room temperature and stirred for 1.5 hours. After the solvent was distilled off under reduced pressure, toluene was added and the mixture was filtered to remove insoluble substances. The filtrate was concentrated under reduced pressure to quantitatively obtain (2-allyloxy-3-tert-butyl-5-methylphenyl)(2,4,5-trimethyl-6-hydrocyclopenta[2,3-b]thiophen-6-yl)dimethylsilane.

$^1$H-NMR (deuterated benzene, δ(ppm)): 0.24(s, 3H), 0.35 (s, 3H), 1.49(s, 9H), 1.86(s, 3H), 1.99(s, 3H), 2.20(s, 3H), 2.26(s, 3H), 3.92(s, 1H), 4.34(s, 2H), 5.07–5.10(m, 1H), 5.49–5.55(m, 1H), 5.74–5.86(m, 1H), 6.57(s, 1H), 7.16(s, 1H), 7.28(s, 1H)

Mass spectra (EI, m/z): 424 (M$^+$), 367, 327, 221, 203, 187, 174, 161, 128, 59, 44

Example 4

Synthesis of dimethylsilyl(2,4,5-trimethyl-6-hydrocyclopenta[2,3-b]thiophen-6-yl)(3-tert-butyl-5-methyl-2-phenoxy)titanium dichloride [Complex 2]

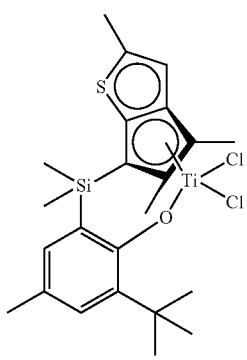

[Complex 2]

A 1.58 M solution of n-butyllithium in hexane (2.21 mL, 3.49 mmol) was added dropwise to a solution of (2-allyloxy-3-tert-butyl-5-methylphenyl)(2,4,5-trimethyl-6-hydrocyclopenta[2,3-b]thiophen-6-yl)dimethylsilane (0.66 g, 1.55 mmol) and triethylamine (0.71 g, 6.98 mmol) in toluene (7.0 mL) at −78° C. and stirred for 10 minutes and then at room temperature for 2 hours. A solution of titanium tetrachloride (0.44 g, 2.33 mmol) in toluene (4.5 mL) was added dropwise to the reaction mixture at −78° C. and stirred at room temperature for 5 hours. The reaction mixture was concentrated and then filtered using hexane to remove insoluble substances. After the solvent was distilled off under reduced pressure, the residue was washed with pentane to obtain dimethylsilyl(2,4,5-trimethyl-6-hydrocyclopenta[2,3-b]thiophen-6-yl)(3-tert-butyl-5-methyl-2-phenoxy)titanium dichloride (0.07 g, 9.2%) as an orange solid.

$^1$H-NMR (deuterated benzene, δ(ppm)): 0.45(s, 3H), 0.55 (s, 3H), 1.53(s, 9H), 1.90(s, 3H), 2.04(s, 3H), 2,24(s, 3H), 2.29(s, 3H), 6.35(s, 1H), 7.18(s, 1H), 7.24(s, 1H)

Mass spectra (EI, m/z): 500 (M$^+$), 484, 449, 433

Example 5

Synthesis of (2-allyloxy-3-tert-butyl-5-methylphenyl)(2,4,5-trimethyl-6-hydrocyclopenta[2,3-b]thiophen-6-yl)diethylsilane

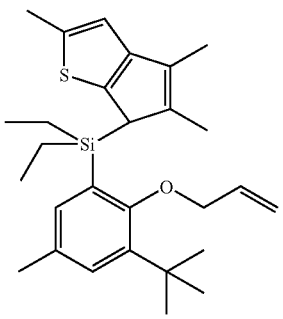

A solution of (2-allyloxy-3-tert-buyl-5-methylphenyl)chlorodiethylsilane (0.91 g, 2.80 mmol) in toluene (2 mL) was added dropwise to a solution of (2,4,5-trimethyl-6-hydrocyclopenta[2,3-b]thiophen-6-yl)lithium (0.50 g, 2.94 mmol) in tetrahydrofuran (20 mL) at −78° C. The resulting reaction mixture was warmed to room temperature and stirred for 5 hours. After the solvent was distilled off under reduced pressure, toluene was added and the mixture was filtered to remove insoluble substances. The filtrate was concentrated under reduced pressure to quantitatively obtain (2-allyloxy-3-tert-butyl-5-methylphenyl)(2,4,5-trimethyl-6-hydrocyclopenta[2,3-b]thiophen-6-yl)diethylsilane.

$^1$H-NMR (deuterated benzene, δ(ppm)): 0.81–1.08(m, 10H), 1.49(s, 9H), 1.93(s, 3H), 1.99(s, 3H), 2.21(s, 3H), 2,27(s, 3H), 4.02(s, 1H), 4.33–4.40(m, 2H), 5.05–5.11(m, 1H), 5.55–5.58(m, 1H), 5.73–5.89(m, 1H), 6.56(s, 1H), 7.19(s, 1H), 7.28(s, 1H)

Mass spectra (EI, m/z): 452(M$^+$), 423, 367, 288, 204, 189, 175, 161, 147, 75, 57, 44

Example 6

Synthesis of diethylsilyl(2,4,5-trimethyl-6-hydrocyclopenta[2,3-b]thiophen-6-yl)(3-tert-butyl-5-methyl-2-phenoxy)titanium dichloride [Complex 3]

[Complex 3]

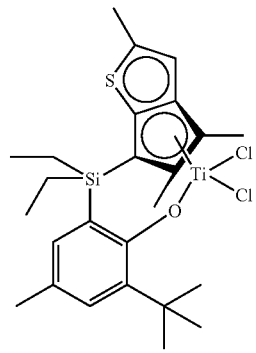

A 1.57 M solution of n-butyllithium in hexane (3.30 mL, 5.18 mmol) was added dropwise to a solution of (2-allyloxy-3-tert-butyl-5-methylphenyl)(2,4,5-trimethyl-6-hydrocyclopenta[2,3-b]thiophen-6-yl)diethylsilane (1.04 g, 2.30 mmol) and triethylamine (1.05 g, 10.35 mmol) in toluene (10.0 mL) at −78° C. and stirred for 10 minutes and then at room temperature for 3.5 hours. A solution of titanium tetrachloride (0.66 g, 3.45 mmol) in toluene (6.9 mL) was added dropwise to the reaction mixture at −78° C. and stirred at room temperature for 5 hours. After the reaction mixture was concentrated and filtered using hexane to remove insoluble substances, the solvent distilled off under reduced pressure. The residue was washed with pentane to obtain diethylsilyl (2,4,5-trimethyl-6-hydrocyclopenta[2,3-b]thiophen-6-yl)(3-tert-butyl-5-methyl-2-phenoxy)titanium dichloride (0.13 g, 10.9%) as an orange solid.

$^1$H-NMR (deuterated benzene, δ(ppm)): 0.80–1.03(m, 6H), 1.03–1.30(m, 4H), 1.53(s, 9H), 1.97(s, 3H), 2.02(s, 3H), 2.24(s, 3H), 2.30(s, 3H), 6.36(s, 1H), 7.19(s, 1H), 7.26(s, 1H)

Mass spectra (EI, m/z): 528 (M$^+$), 499, 477

Example 7

Synthesis of (2-allyloxy-3-tert-butyl-5-methylphenyl)(2,5-dimethylcyclopenta[1,2-b:4,3-b']dithiophen-7-yl)dimethylsilane

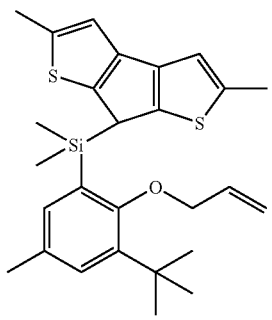

A solution of (2-allyloxy-3-tert-buyl-5-methylphenyl)chlorodimethylsilane (0.71 g, 2.40 mmol) in toluene (4 mL) was added dropwise to a solution of (2,5-dimethylcyclopenta[1,2-b:4,3-b']dithiophen-7-yl)lithium (0.51 g, 2.40 mmol) in tetrahydrofuran (10 mL) at −78° C. The resulting reaction mixture was warmed to room temperature and stirred for 5 hours. After the solvent was distilled off under reduced pressure, hexane was added and the mixture was filtered to remove insoluble substances. The filtrate was concentrated under reduced pressure to quantitatively obtain (2-allyloxy-3-tert-butyl-5-methylphenyl)(2,5-dimethylcyclopenta[1,2-b:4,3-b']dithiophen-7-yl)dimethylsilane.

$^1$H-NMR (deuterated benzene, δ(ppm)): 0.28(s 6H), 1.53 (s, 9H), 2.21(s, 3H), 2.23(s, 6H), 4.30–4.35(m, 2H), 4.43(s, 1H), 4.99–5.03(m, 1H), 5.46–5.57(m, 1H), 5.63–5.79(m, 1H), 6.75(s, 2H), 7.18(s, 1H), 7.32(s, 1H)

Mass spectra (EI, m/z): 466(M$^+$), 261, 233, 205, 73, 57

Example 8

Synthesis of dimethylsilyl(2,5-dimethylcyclopenta[1,2-b:4,3-b']dithiophen-7-yl)(3-tert-butyl-5-methyl-2-phenoxy)titanium dichloride [Complex 4]

[Complex 4]

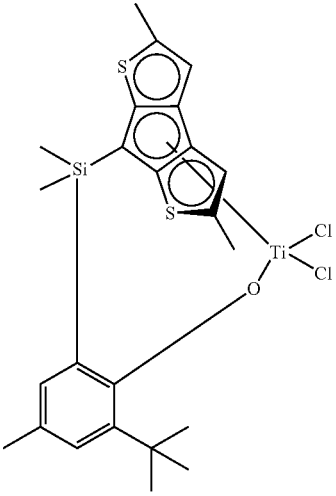

A 1.56 M solution of n-butyllithium in hexane (1.50 mL, 2.34 mmol) was added dropwise to a solution of (2-allyloxy-3-tert-butyl-5-methylphenyl)(2,5-dimethylcyclopenta[1,2-b:4,3-b']dithiophen-7-yl)dimethylsilane (0.45 g, 0.96 mmol) and triethylamine (0.47 g, 4.68 mmol) in toluene (5.0 mL) at −78° C. and stirred for 10 minutes and then at room temperature for 2 hours. A solution of titanium tetrachloride (0.27 g, 1.44 mmol) in toluene (1.5 mL) was added dropwise to the reaction mixture at −78° C. and stirred at room temperature for 5 hours. After the reaction mixture was concentrated and filtered using hexane to remove insoluble substances, the solvent was distilled off under reduced pressure. The residue was washed with pentane to obtain dimethylsilyl(2,5-dimethylcyclopenta[1,2-b:4,3-b']dithiophen-7-yl)(3-tert-butyl-5-methyl-2-phenoxy)titanium dichloride (35.4 mg, 6.8%) as a brown solid.

$^1$H-NMR (deuterated benzene, δ(ppm)): 0.61(s, 6H), 1.49 (s, 9H), 2.05(s, 3H), 2.06(s, 3H), 2.24(s, 3H), 6.67(s, 2H), 7.21(s, 1H), 7.26(s, 1H)

Mass spectra (EI, m/z): 524 (M$^+$), 491, 287, 205, 75, 57

Example 9

Synthesis of (2-allyloxy-3-tert-butyl-5-methylphenyl)(2,5-dimethylcyclopenta[1,2-b:4,3-b']dithiophen-7-yl)diethylsilane

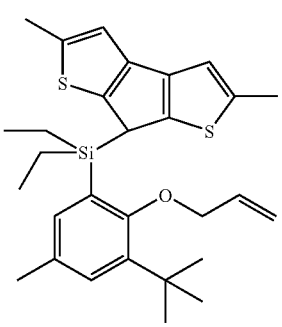

At −78° C., n-butyllithium (1.56 M, 1.69 mL, 2.64 mmol) was added dropwise to a solution of 2,5-dimethylcyclopenta[1,2-b:4,3-b']dithiophen (0.50 g, 2.42 mmol) in tetrahydrofuran (10 mL) and the mixture was stirred at room temperature for 4 hours. After the reaction mixture was cooled to −78° C., a solution of (2-allyloxy-3-tert-buyl-5-methylphenyl)chlorodiethylsilane (0.72 g, 2.20 mmol) in toluene (3 mL) was added dropwise thereto. The resulting reaction mixture was warmed to room temperature and stirred for 2 hours. After the solvent was distilled off under reduced pressure, toluene was added and the mixture was filtered to remove insoluble substances. The filtrate was concentrated under reduced pressure to quantitatively obtain (2-allyloxy-3-tert-butyl-5-methylphenyl)(2,5-dimethylcyclopenta[1,2-b:4,3-b']dithiophen-7-yl)diethylsilane.

$^1$H-NMR (deuterated benzene, δ(ppm)): 0.74–0.92(m, 6H), 0.92–1.07(m, 4H), 1.52(s, 9H), 2.24(s, 6H), 2.25(s, 3H), 4.32–4.40(m, 2H), 4.48(s, 1H), 4.98–5.07(m, 1H), 5.48–5.58(m, 1H), 5.68–5.80(m, 1H), 6.75(s, 2H), 7.26(s, 1H), 7.34(s, 1H)

Mass spectra (EI, m/z): 494 (M$^+$), 289, 261, 2.33, 205, 73, 57

Example 10

Synthesis of diethylsilyl(2,5-dimethylcyclopenta[1,2-b:4,3-b']dithiophen-7-yl)(3-tert-butyl-5-methyl-2-phenoxy)titanium dichloride [Complex 5]

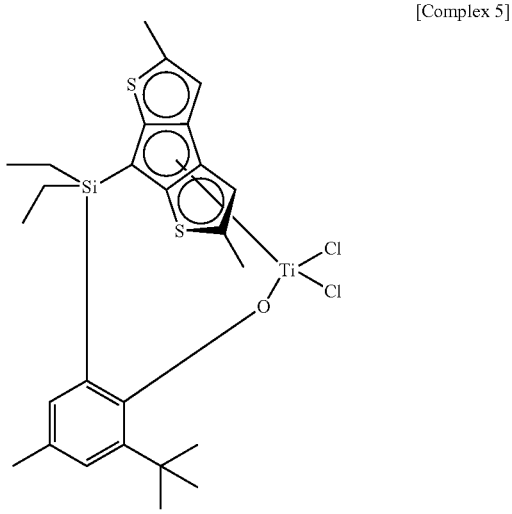

[Complex 5]

A 1.56 M solution of n-butyllithium in hexane (1.77 mL, 2.77 mmol) was added dropwise to a solution of (2-allyloxy-3-tert-butyl-5-methylphenyl)(2,5-dimethylcyclopenta[1,2-b:4,3-b']dithiophen-7-yl)diethylsilane (0.61 g, 1.23 mmol) and triethylamine (0.56 g, 5.54 mmol) in toluene (7.0 mL) at −78° C. and stirred for 10 minutes and then at room temperature for 2 hours. A solution of titanium tetrachloride (0.35 g, 1.85 mmol) in toluene (3 mL) was added dropwise to the reaction mixture at −78° C. and stirred at room temperature for 5 hours. After the reaction mixture was concentrated and filtered using hexane to remove insoluble substances, the solvent was distilled off under reduced pressure. The residue was washed with pentane to obtain diethylsilyl(2,5-dimethylcyclopenta[1,2-b:4,3-b']dithiophen-7-yl)(3-tert-butyl-5-methyl-2-phenoxy)titanium dichloride (71.0 mg, 10.1%) as a brown solid.

$^1$H-NMR (deuterated benzene, δ(ppm)): 1.01–1.07(m, 6H), 1.14–1.28(m, 4H), 1.49(s, 9H), 2.04(s, 6H), 2.24(s, 3H), 6.67(s, 2H), 7.25(s, 1H), 7.28(s, 1H)

Mass spectra (EI, m/z): 570 (M$^+$), 541, 519

Example 11

Synthesis of (2-dimethylamino-4,5-dimethylcyclopentadienyl)(2-allyloxy-3-tert-butyl-5-methylphenyl)dimethylsilane

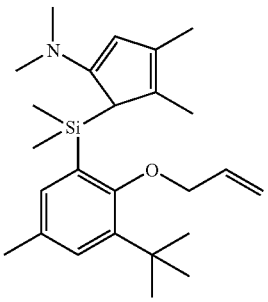

Under nitrogen atmosphere, after a solution of 3,4-dimethylcyclopentenone (15.0 mmol) in toluene (10.0 mL) was cooled to −78° C., a solution of tetrakisdimethylaminotitanium (7.8 mmol) in toluene(8.3 mL) was added dropwise and the mixture was stirred at room temperature. After disappearance of ketone from the reaction mixture was confirmed by gas chromatography, the solvent was distilled off under reduced pressure. Hexane (18.3 mL) was added and a precipitated solid was separated by filtration. The filtrate was concentrated to obtain 1-dimethylamino-3,4-dimethylcyclopentadiene (2.23 g) as an oil. The oil was added to hexane (30.0 mL) without being purified and cooled to −78° C. A 1.59 M solution of n-butyl lithium in hexane (15.0 mmol) was added dropwise. The mixture was warmed to room temperature and stirred for 4 hours. A formed solid was separated by filtration and dried to obtain 1-dimethylamino-3,4-dimethylcyclopentadienyllithium (0.63 g, 29.6%) as flesh powder.

$^1$H-NMR (deuterated chloroform, δ(ppm)): 1.86(3H), 1.90(3H), 2.41(6H), 2.66(2H), 4.94(1H)

Mass spectra (EI, m/z): 137 (M$^+$), 122, 77

A solution of (2-allyloxy-3-tert-butyl-5-methylphenyl)dimethylchlorosilane (7.0 mmol) in toluene (12.1 mL) was added dropwise to a solution of 1-dimethylamino-3,4-dimethylcyclopentadienyllithium (7.0 mmol) in tetrahydrofuran (10.5 mL) and the mixture was stirred at room temperature for 6 hours. After the solvent was distilled off under reduced pressure, dehydrated pentane was added and a precipitated solid was filtered off. The filtrate was concentrated to obtain the title compound (2.86 g, 100%) as an oil.

$^1$H-NMR (deuterated benzene, δ(ppm)): 0.36(3H), 0.59 (3H), 1.71(9H), 1.90(3H), 2.21(3H), 2.44(6H), 3.67(1H), 4.40–4.47(2H), 5.10–5.14(1H), 5.27(1H), 5.54–5.60(1H), 5.79–5.88(1H), 7.24(1H), 7.28(1H)

Mass spectra (EI, m/z): 397 (M$^+$), 382, 340, 261, 136

Example 12

Synthesis of dimethylsilyl(2-dimethylamino-4,5-dimethylcyclopentadienyl)(3-tert-butyl-5-methyl-2-phenoxy)titanium dichloride [Complex 6]

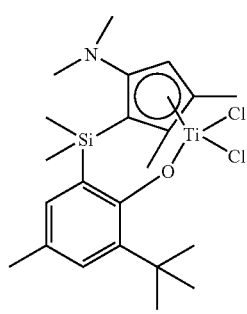

[Complex 6]

A 1.56 M solution of n-butyllithium in hexane (8.0 mmol) was added dropwise to a solution of (2-dimethylamino-4,5-dimethylcyclopentadienyl)(2-allyloxy-3-tert-butyl-5-methylphenyl)dimethylsilane (2.0 mmol) and triethylamine (16.0 mmol) in toluene (15.6 mL) at −78° C. and the mixture was warmed to room temperature and then stirred for 1 hour. The reaction mixture was added dropwise to a solution of titanium tetrachloride (6.0 mmol) in toluene (10.1 mL) at −78° C. The resulting reaction mixture was stirred at room temperature for 5 hours to obtain a red solution. The solvent of the solution was replaced with hexane and a precipitated solid was filtered off. The filtrate was concentrated to obtain an oil, which was recrystallized from pentane to obtain the title compound (32.6 mg, 3.4%) as a black solid.

$^1$H-NMR (deuterated benzene, δ(ppm)): 0.45(3H), 0.52(3H), 1.57(9H), 1.82(3H), 2.14(3H), 2.25(3H), 2.38(6H), 5.90(1H), 7.16(1H), 7.29(1H)

Mass spectra (EI, m/z): 397 (M$^+$), 382, 340, 261, 136

«Homopolymerization of Ethylene»

Example 13

<Polymerization Condition A-1>

An autoclave was charged with toluene (5.0 mL) under nitrogen atmosphere and the temperature was stabilized at 40° C. It was then charged with ethylene until it was pressurized to 0.60 MPa, and the pressure was stabilized. Thereto MMAO (5.8 wt % Al, Tosoh-Akzo Corporation) (100 μmol) and the Complex 2 (0.10 μmol) were added to carry out polymerization for 30 min. As a result of polymerization, a polymer was produced in an amount of 9.2×10$^6$ g per 1 mol of titanium and per an hour.

Example 14

<Polymerization Condition B-1>

Polymerization was carried out in the same manner as Example 13, except that a solution of triisobutylaluminum in hexane (40 μL, 1.0 M, Kanto Chemical Co., Ltd.) and pentafluorophenylborane (0.30 μmol) were used in place of MMAO. As a result of polymerization, a polymer was produced in an amount of 1.6×10$^6$ g per 1 mol of titanium and per an hour.

Example 15

<Polymerization Condition C-1>

Polymerization was carried out in the same manner as Example 13, except that a solution of triisobutylaluminum in hexane (40 μL, 1.0 M, Kanto Chemical Co., Ltd.) and dimethylanilinium tetrakis(pentafluorophenyl)borate (0.30 μmol) were used in place of MMAO. As a result of polymerization, a polymer was produced in an amount of 11.4×10$^6$ g per 1 mol of titanium and per an hour.

Example 16

<Polymerization Condition D-1>

Polymerization was carried out in the same manner as Example 13, except that a solution of triisobutylaluminum in hexane (40 μL, 1.0 M, Kanto Chemical Co., Ltd.) and triphenylmethyl tetrakis(pentafluorophenyl)borate (0.30 μmol) were used in place of MMAO. As a result of polymerization, a polymer was produced in an amount of 5.2×10$^6$ g per 1 mol of titanium and per an hour.

«Copolymerization of Ethylene/1-Hexene»

Example 17

<Polymerization Condition A-2>

An autoclave was charged with toluene (5.0 mL) and 1-hexene (50 μL) under nitrogen atmosphere and the temperature was stabilized at 40° C. It was then charged with ethylene until it was pressurized to 0.60 MPa, and the pressure was stabilized. Thereto MMAO (5.8 wt % Al, Tosoh-Akzo Corporation) (100 μmol) and the Complex 2 (0.10 μmol) were added to carry out polymerization for 30 min. As a result of polymerization, a polymer having the molecular weight (Mw)=739,000, the molecular weight distribution (Mw/Mn)=2.0, Tm=102.8° C. and SCB=6 was produced in an amount of 7.0×10$^6$ g per 1 mol of titanium and per an hour.

Example 18

<Polymerization Condition A-3>

Polymerization was carried out in the same manner as Example 17, except that the polymerization temperature was 70° C. As a result of polymerization, a polymer having the molecular weight (Mw)=222,000, the molecular weight distribution (Mw/Mn)=1.8, Tm=98.7° C. and SCB=7 was produced in an amount of 40.9×10$^6$ g per 1 mol of titanium and per an hour.

Example 19

<Polymerization Condition B-2>

An autoclave was charged with toluene (5.0 mL) and 1-hexene (50 μL) under nitrogen atmosphere and the temperature was stabilized at 40° C. It was then charged with ethylene until it was pressurized to 0.60 MPa, and the pressure was stabilized. Thereto a solution of triisobutylaluminum in hexane (40 μL, 1.0 M, Kanto Chemical Co., Ltd.), pentafluorophenylborane (0.30 μmol) and the Complex 2 (0.10 μmol) were added to carry out polymerization for 30 min. As a result of polymerization, a polymer having the molecular weight (Mw)=904,000, the molecular weight distribution (Mw/Mn)=1.7 and Tm=100.2° C. was produced in an amount of $1.1 \times 10^6$ g per 1 mol of titanium and per an hour.

Example 20

<Polymerization Condition B-3>

Polymerization was carried out in the same manner as Example 19, except that the polymerization temperature was 70° C. As a result of polymerization, a polymer having the molecular weight (Mw)=575,000, the molecular weight distribution (Mw/Mn)=1.7, Tm=103.9° C. and SCB=24 was produced in an amount of $2.1 \times 10^6$ g per 1 mol of titanium and per an hour.

Example 21

<Polymerization Condition C-2>

An autoclave was charged with toluene (5.0 mL) and 1-hexene (50 μL) under nitrogen atmosphere and the temperature was stabilized at 40° C. It was then charged with ethylene until it was pressurized to 0.60 MPa, and the pressure was stabilized. Thereto a solution of triisobutylaluminum in hexane (40 μL, 1.0 M, Kanto Chemical Co., Ltd.), dimethylanilinium tetrakis(pentafluorophenyl)borate (0.30 μmol) and the Complex 2 (0.10 μmol) were added to carry out polymerization for 30 min. As a result of polymerization, a polymer having the molecular weight (Mw)=1,048,000, the molecular weight distribution (Mw/Mn)=2.7, Tm=114.3° C. and SCB=16 was produced in an amount of $129.5 \times 10^6$ g per 1 mol of titanium and per an hour.

Example 22

<Polymerization Condition C-3>

Polymerization was carried out in the same manner as Example 21, except that the polymerization temperature was 70° C. As a result of polymerization, a polymer having the molecular weight (Mw)=648,000, the molecular weight distribution (Mw/Mn)=2.0, Tm=108.4° C. and SCB=18 was produced in an amount of $74.3 \times 10^6$ g per 1 mol of titanium and per an hour.

Example 23

<Polymerization Condition C-4>

Polymerization was carried out in the same manner as Example 21, except that the polymerization temperature was 130° C. and 4 μL of the solution of triisobutylaluminum in hexane was used. As a result of polymerization, a polymer having the molecular weight (Mw)=250,000, the molecular weight distribution (Mw/Mn)=2.2, Tm=104.3° C. and SCB=24 was produced in an amount of $3.2 \times 10^6$ g per 1 mol of titanium and per an hour.

Example 24

<Polymerization Condition D-2>

An autoclave was charged with toluene (5.0 mL) and 1-hexene (50 μL) under nitrogen atmosphere and the temperature was stabilized at 40° C. It was then charged with ethylene until it was pressurized to 0.60 MPa, and the pressure was stabilized. Thereto a solution of triisobutylaluminum in hexane (40 μL, 1.0 M, Kanto Chemical Co., Ltd.), triphenylmethyl tetrakis(pentafluorophenyl)borate (0.30 μmol) and the Complex 2 (0.10 μmol) were added to carry out polymerization for 30 min. As a result of polymerization, a polymer having the molecular weight (Mw)=1,104,000, the molecular weight distribution (Mw/Mn)=3.1, Tm=118.8° C. and SCB=14 was produced in an amount of $56.6 \times 10^6$ g per 1 mol of titanium and per an hour.

Example 25

<Polymerization Condition D-3>

Polymerization was carried out in the same manner as Example 24, except that the polymerization temperature was 70° C. As a result of polymerization, a polymer having the molecular weight (Mw) 767,000, the molecular weight distribution (Mw/Mn)=2.8, Tm=107.3° C. and SCB=23 was produced in an amount of $77.4 \times 10^6$ g per 1 mol of titanium and per an hour.

Example 26

<Polymerization Condition D-4>

Polymerization was carried out in the same manner as Example 24, except that the polymerization temperature was 130° C. and 4 μL of the solution of triisobutylaluminum in hexane was used. As a result of polymerization, a polymer having the molecular weight (Mw)=282,000, the molecular weight distribution (Mw/Mn)=3.1, Tm=101.5° C. and SCB=30 was produced in an amount of $56.6 \times 10^6$ g per 1 mol of titanium and per an hour.

Example 27

<Polymerization Condition A-5>

Polymerization was carried out in the same manner as Example 17, except that 60 μL of 1-hexene was charged and the Complex 5 was used. As a result of polymerization, a polymer having the molecular weight (Mw)=744,000, the molecular weight distribution (Mw/Mn)=2.1, Tm=93.5° C. and SCB=14 was produced in an amount of $14.4 \times 10^6$ g per 1 mol of titanium and per an hour.

Example 28

<Polymerization Condition B-5>

Polymerization was carried out in the same manner as Example 19, except that 60 μL of 1-hexene was charged and the Complex 4 was used. As a result of polymerization, a polymer having the molecular weight (Mw)=903,000, the molecular weight distribution (Mw/Mn)=1.5 and Tm=89.1° C. was produced in an amount of $1.7 \times 10^6$ g per 1 mol of titanium and per an hour.

Example 29

<Polymerization Condition C-5>

Polymerization was carried out in the same manner as Example 21, except that 60 μL of 1-hexene was charged and the Complex 4 was used. As a result of polymerization, a polymer having the molecular weight (Mw)=988,000, the molecular weight distribution (Mw/Mn)=2.1, Tm=112.4° C. and SCB=32 was produced in an amount of $113.2 \times 10^6$ g per 1 mol of titanium and per an hour.

Example 30

<Polymerization Condition C-6>

Polymerization was carried out in the same manner as Example 23, except that 40 μL of 1-hexene was charged and the Complex 4 was used. As a result of polymerization, a polymer having the molecular weight (Mw)=272,000, the molecular weight distribution (Mw/Mn)=2.1, Tm=101.2° C. and SCB=30 was produced in an amount of $26.7 \times 10^6$ g per 1 mol of titanium and per an hour.

Example 31

<Polymerization Condition D-5>

Polymerization was carried out in the same manner as Example 24, except that 60 μL of 1-hexene was charged and the Complex 4 was used. As a result of polymerization, a polymer having the molecular weight (Mw)=408,000, the molecular weight distribution (Mw/Mn)=1.9, Tm=109.8° C. and SCB=18 was produced in an amount of $41.3 \times 10^6$ g per 1 mol of titanium and per an hour.

Example 32

<Polymerization Condition D-6>

Polymerization was carried out in the same manner as Example 26, except that 40 μL of 1-hexene was charged and the Complex 4 was used. As a result of polymerization, a polymer having the molecular weight (Mw)=255,000, the molecular weight distribution (Mw/Mn)=2.0, Tm=102.4° C. and SCB=24 was produced in an amount of $7.0 \times 10^6$ g per 1 mol of titanium and per an hour.

The following tables 1 to 5 show the catalytic components, polymerization conditions, catalytic activity and reaction results of Examples 13 to 91 and those in Comparative Examples 1 to 9 using dimethylsilyl(tetramethylcyclopentadienyl)(3-tert-butyl-5-methyl-2-phenoxy)titanium dichloride [Complex 7].

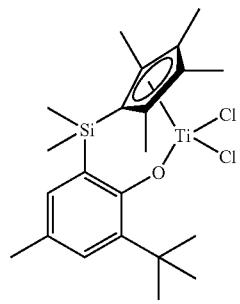

[Complex 7]

TABLE 1

Ethylene Homopolymerization

| Example | Complex | Polymerization condition | Activity*[1] |
|---|---|---|---|
| 33 | 1 | A-1 | 0.6 |
| 34 | 1 | B-1 | 0.3 |
| 35 | 1 | C-1 | 3.4 |
| 36 | 1 | D-1 | 4.0 |
| 13 | 2 | A-1 | 9.2 |
| 14 | 2 | B-1 | 1.6 |
| 15 | 2 | C-1 | 11.4 |
| 16 | 2 | D-1 | 5.2 |
| 37 | 3 | A-1 | 8.6 |
| 38 | 3 | B-1 | 4.7 |
| 39 | 3 | C-1 | 59.5 |
| 40 | 3 | D-1 | 4.5 |
| 41 | 4 | A-1 | 1.9 |
| 42 | 4 | B-1 | 1.9 |
| 43 | 4 | C-1 | 55.0 |
| 44 | 4 | D-1 | 10.2 |
| 45 | 5 | A-1 | 11.3 |
| 46 | 5 | B-1 | 3.3 |
| 47 | 5 | C-1 | 37.4 |
| 48 | 5 | D-1 | 5.4 |
| 49 | 6 | A-1 | 1.3 |
| 50 | 6 | B-1 | 2.8 |
| 51 | 6 | C-1 | 5.3 |
| 52 | 6 | D-1 | 5.0 |

*[1] ($\times 10^6$ gPE/mol-cat/hr)

TABLE 2

Ethylene/1-Hexene Copolymerization (MMAO)

| Example | Complex | Polymerization condition | Temperature (° C.) | Activity*[1] | Mw | Mw/Mn | Tm(° C.) | SCB*[2] |
|---|---|---|---|---|---|---|---|---|
| 17 | 2 | A-2 | 40 | 7.0 | 739,000 | 2.0 | 102.8 | 6 |
| 18 | 2 | A-3 | 70 | 40.9 | 222,000 | 1.8 | 98.7 | 7 |
| 53 | 3 | A-2 | 40 | 6.3 | 651,000 | 2.0 | 105.8 | 4 |
| 54 | 3 | A-3 | 70 | 39.7 | 164,000 | 2.2 | 101.8 | 15 |
| 55 | 4 | A-3 | 70 | 91.4 | 197,000 | 1.8 | 95.8 | 20 |

TABLE 2-continued

Ethylene/1-Hexene Copolymerization (MMAO)

| | Complex | Polymerization condition | Temperature (° C.) | Activity*[1] | Mw | Mw/Mn | Tm(° C.) | SCB*[2] |
|---|---|---|---|---|---|---|---|---|
| 27 | 5 | A-5 | 40 | 14.4 | 744,000 | 2.1 | 93.5 | 14 |
| 56 | 5 | A-3 | 70 | 76.5 | 226,000 | 2.0 | 97.8 | 14 |
| 57 | 6 | A-5 | 40 | 1.5 | 532,000 | 2.0 | 109.0 | 6 |
| 58 | 6 | A-3 | 70 | 1.6 | 144,000 | 1.6 | 113.0 | 9 |
| Comparative Example | | | | | | | | |
| 1 | 7 | A-3 | 70 | 14.3 | 128,000 | 3.2 | 91.1 | 23 |

*[1]($\times 10^6$ gPE/mol-cat/hr)
*[2]The number of branched methyl groups per 1,000 carbon atoms of a polymer.

TABLE 3

Ethylene/1-Hexene Copolymerization (TIBA/B($C_6F_5$)$_3$)

| | Complex | Polymerization condition | Temperature (° C.) | Activity*[1] | Mw | Mw/Mn | Tm(° C.) | SCB*[2] |
|---|---|---|---|---|---|---|---|---|
| Example | | | | | | | | |
| 19 | 2 | B-2 | 40 | 1.1 | 904,000 | 1.7 | 100.2 | ND |
| 20 | 2 | B-3 | 70 | 2.1 | 575,000 | 1.7 | 103.9 | 24 |
| 59 | 3 | B-2 | 40 | 2.3 | 733,000 | 1.9 | 105.4 | 11 |
| 60 | 3 | B-3 | 70 | 2.2 | 439,000 | 1.8 | 98.6 | ND |
| 28 | 4 | B-5 | 40 | 1.7 | 903,000 | 1.5 | 89.1 | ND |
| 61 | 4 | B-3 | 70 | 2.1 | 360,000 | 1.5 | 91.9 | ND |
| 62 | 5 | B-5 | 40 | 12.4 | 1,046,000 | 1.7 | 87.5 | 20 |
| 63 | 5 | B-3 | 70 | 2.3 | 499,000 | 1.5 | 83.2 | 15 |
| 64 | 6 | B-5 | 40 | 2.6 | 1,341,000 | 1.5 | 105.5 | 8 |
| 65 | 6 | B-3 | 70 | 1.0 | 510,000 | 1.5 | 104.4 | 7 |
| Comparative Example | | | | | | | | |
| 2 | 7 | B-2 | 40 | 1.2 | 566,000 | 2.8 | 85.6 | 24 |
| 3 | 7 | B-3 | 70 | 1.0 | 333,000 | 2.2 | 83.7 | 19 |

*[1]($\times 10^6$ gPE/mol-cat/hr)
*[2]The number of branched methyl groups per 1,000 carbon atoms of a polymer.
ND: undone

TABLE 4

Ethylene/1-Hexene Copolymerization (TIBA/AB)

| | Complex | Polymerization condition | Temperature (° C.) | Activity*[1] | Mw | Mw/Mn | Tm(° C.) | SCB*[2] |
|---|---|---|---|---|---|---|---|---|
| Example | | | | | | | | |
| 66 | 1 | C-2 | 40 | 6.9 | 556,000 | 2.7 | 101.3 | 8 |
| 67 | 1 | C-3 | 70 | 48.1 | 289,000 | 2.8 | 102.8 | 9 |
| 68 | 1 | C-4 | 130 | 45.3 | 379,000 | 3.0 | 105.9 | 12 |
| 21 | 2 | C-2 | 40 | 129.5 | 1,048,000 | 2.7 | 114.3 | 16 |
| 22 | 2 | C-3 | 70 | 74.3 | 648,000 | 2.0 | 108.4 | 18 |
| 23 | 2 | C-4 | 130 | 3.2 | 250,000 | 2.2 | 104.3 | 24 |
| 69 | 3 | C-2 | 40 | 282.1 | 987,000 | 2.7 | 110.9 | 12 |
| 70 | 3 | C-3 | 70 | 32.2 | 758,000 | 5.1 | 112.6 | 33 |
| 71 | 3 | C-4 | 130 | 31.8 | 228,000 | 3.5 | 104.2 | 27 |
| 29 | 4 | C-5 | 40 | 113.2 | 988,000 | 2.1 | 112.4 | 32 |
| 72 | 4 | C-3 | 70 | 58.1 | 323,000 | 1.9 | 109.2 | 40 |
| 30 | 4 | C-6 | 130 | 26.7 | 272,000 | 2.1 | 101.2 | 30 |
| 73 | 5 | C-5 | 40 | 49.2 | 913,000 | 2.1 | 109.5 | 23 |
| 74 | 5 | C-3 | 70 | 20.4 | 812,000 | 1.8 | 127.6 | 15 |
| 75 | 5 | C-6 | 130 | 27.5 | 268,000 | 2.0 | 99.3 | 23 |
| 76 | 6 | C-5 | 40 | 4.9 | 936,000 | 2.2 | 101.5 | 14 |
| 77 | 6 | C-3 | 70 | 8.6 | 547,000 | 1.8 | 105.2 | 10 |
| 78 | 6 | C-6 | 130 | 10.1 | 360,000 | 1.6 | 103.5 | 6 |

TABLE 4-continued

Ethylene/1-Hexene Copolymerization (TIBA/AB)

| | Complex | Polymerization condition | Temperature (° C.) | Activity*1 | Mw | Mw/Mn | Tm(° C.) | SCB*2 |
|---|---|---|---|---|---|---|---|---|
| Comparative Example | | | | | | | | |
| 4 | 7 | C-2 | 40 | 26.3 | 654,000 | 2.6 | 98.2 | 19 |
| 5 | 7 | C-3 | 70 | 152.3 | 260,000 | 2.5 | 88.0 | 28 |
| 6 | 7 | C-4 | 130 | 30.8 | 169,000 | 2.1 | 90.3 | 24 |

*1($\times 10^6$ gPE/mol-cat/hr)
*2The number of branched methyl groups per 1,000 carbon atoms of a polymer.

TABLE 5

Ethylene/1-Hexene Copolymerization (TIBA/CB)

| | Complex | Polymerization condition | Temperature (° C.) | Activity*1 | Mw | Mw/Mn | Tm(° C.) | SCB*2 |
|---|---|---|---|---|---|---|---|---|
| Example | | | | | | | | |
| 79 | 1 | D-2 | 40 | 9.4 | 522,000 | 2.2 | 100.9 | 10 |
| 80 | 1 | D-3 | 70 | 24.1 | 362,000 | 2.6 | 104.1 | 11 |
| 81 | 1 | D-4 | 130 | 13.6 | 380,000 | 2.8 | 107.3 | 12 |
| 24 | 2 | D-2 | 40 | 56.6 | 1,104,000 | 3.1 | 118.8 | 14 |
| 25 | 2 | D-3 | 70 | 77.4 | 767,000 | 2.8 | 107.3 | 23 |
| 26 | 2 | D-4 | 130 | 2.3 | 282,000 | 3.1 | 101.5 | 30 |
| 82 | 3 | D-2 | 40 | 303.0 | 923,000 | 2.3 | 112.5 | 17 |
| 83 | 3 | D-3 | 70 | 20.1 | 679,000 | 5.2 | 108.1 | 21 |
| 84 | 3 | D-4 | 130 | 10.0 | 229,000 | 4.1 | 103.5 | 29 |
| 31 | 4 | D-5 | 40 | 41.3 | 408,000 | 1.9 | 109.8 | 18 |
| 85 | 4 | D-3 | 70 | 76.3 | 348,000 | 1.8 | 118.6 | 41 |
| 32 | 4 | D-6 | 130 | 7.0 | 255,000 | 2.0 | 102.4 | 24 |
| 86 | 5 | D-5 | 40 | 223.9 | 909,000 | 2.0 | 130.1 | 11 |
| 87 | 5 | D-3 | 70 | 19.6 | 481,000 | 2.0 | 112.2 | 17 |
| 88 | 5 | D-6 | 130 | 9.1 | 301,000 | 2.4 | 98.8 | 24 |
| 89 | 6 | D-5 | 40 | 15.5 | 615,000 | 2.2 | 105.4 | 17 |
| 90 | 6 | D-3 | 70 | 13.4 | 514,000 | 1.8 | 105.2 | 8 |
| 91 | 6 | D-6 | 130 | 8.7 | 409,000 | 1.6 | 106.3 | 6 |
| Comparative Example | | | | | | | | |
| 7 | 7 | D-2 | 40 | 59.1 | 535,000 | 6.7 | 112.7 | 17 |
| 8 | 7 | D-3 | 70 | 75.3 | 357,000 | 3.6 | 118.0 | 12 |
| 9 | 7 | D-4 | 130 | 9.5 | 189,000 | 2.7 | 89.4 | 28 |

*1($\times 10^6$ gPE/mol-cat/hr).
*2The number of branched methyl groups per 1,000 carbon atoms of a polymer.

Example 92

Synthesis of ethyl (2Z)-2-methyl-3-[5-methylthiophen-2-yl]-2-propenoate

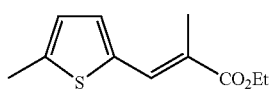

Under nitrogen atmosphere, a reactor was loaded with 60% sodium hydride (87.1 g, 2.15 mol) and dry THF (130 mL). A solution of triethyl 2-phosphonopropionate (239 mL, 1.54 mol) in dry THF(160 mL) was added dropwise into the reactor in an ice bath. The mixture was stirred at room temperature for 1.5 hours, and successively, in an ice bath, a solution of 5-methylthiophene-2-carboxyaldehyde (180.0 g, 1.43 mol) in dry THF (430 mL) was added dropwise thereto under ice bath cooling and stirred at room temperature for 5 hours. An aqueous saturated ammonium chloride solution was added to the resulting reaction mixture and the mixture was extracted with diethyl ether to obtain an organic layer. The organic layer was washed with a saturated brine and dried over magnesium sulfate anhydride. The solvent was distilled off under reduced pressure to obtain ethyl (2Z)-2-methyl-3-[5-methylthiophen-2-yl]-2-propenoate (291.8 g, 97.0%) as a dark red liquid.

Example 93

Synthesis of methyl 2-methyl-3-[5-methylthiophen-2-yl]-2-propanoate

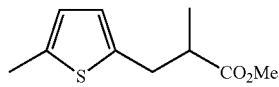

Under nitrogen atmosphere, a reactor was loaded with ethyl (2Z)-2-methyl-3-[5-methylthiophen-2-yl]-2-propenoate (20.0 g, 95.1 mmol) and dry methanol (100 mL) and magnesium (7.0 g, 289.0 mmol) was added in small portions and gradually thereto. The mixture was stirred for 5 hours, acidified by addition of an aqueous 3N hydrochloric acid solution and then extracted with ethyl acetate to obtain an organic layer. The organic layer was washed with saturated brine and dried over anhydrous magnesium sulfate. The solvent was distilled off under reduced pressure to obtain a dark red liquid. The liquid was purified by silica gel chromatography (hexane/ethyl acetate=10/1) to obtain methyl 2-methyl-3-[5-methylthiophen-2-yl]-2-propanoate (11.2 g, 59.4%) as a pale yellow liquid.

Example 94

Synthesis of 2-methyl-3-[5-methylthiophen-2-yl]-2-propanoic acid

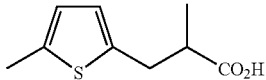

Under nitrogen atmosphere, a reactor was loaded with methyl 2-methyl-3-[5-methylthiophen-2-yl]-2-propanoate (162.9 g, 0.82 mmol) and Claisen reagent*(391 mL) and the mixture was stirred at room temperature for 1 hour. The reaction mixture was adjusted to pH 1–2 by addition of an aqueous 6N hydrochloric acid solution and then extracted with ethyl acetate to obtain an organic layer. The organic layer was washed with saturated brine and dried over anhydrous magnesium sulfate. The solvent was distilled off under reduced pressure to obtain 2-methyl-3-[5-methylthiophen-2-yl]-2-propanoic acid (149.6 g, 99.0%) as a pale yellow oil.
*Claisen reagent: a solution of potassium hydroxide (35 g) in a mixed solvent of water (25 mL) and methanol (100 mL)

Example 95

Synthesis of 2,5-dimethyl-5,6-dihydrocyclopenta[1,2-b]thiophen-4-one

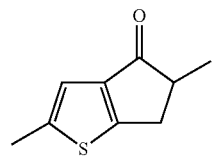

Under nitrogen atmosphere, a reactor was loaded with polyphosphoric acid (72.1 g) and phosphorus pentoxide (72.1 g, 0.51 mol) was added thereto and stirred at 140° C. for 1 hour. Then, a solution of 2-methyl-3-[5-methylthiophen-2-yl]propanoic acid (43.0 g, 0.23 mol) in 1,2-dichloroethane (75 mL) was added dropwise and stirred at 100° C. for 2 hours. The reaction mixture was added to iced water (1,000 mL) with stirring and after 30 minutes, extracted with chloroform to obtain an organic layer. The organic layer was washed with an aqueous saturated sodium carbonate solution and dried over anhydrous magnesium sulfate. The solvent was distilled off under reduced pressure to obtain a black oil. The oil was purified by silica gel chromatography (hexane/ethyl acetate=5/1) to obtain 2,5-dimethyl-5,6-dihydrocyclopenta[1,2-b]thiophen-4-one (32.6 g, 84.1%) as a reddish brown oil.

Example 96

Synthesis of 2,4,5-trimethyl-6-hydrocyclopenta[1,2-b]thiophene

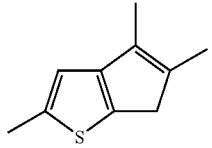

A solution of methyllithium in diethyl ether (1.04 M, Kanto Chemical Co., Ltd.) (31.8 mL, 33.1 mmol) was added dropwise to a solution of 2,5-dimethyl-5,6-dihydrocyclopenta[1,2-b]thiophen-4-one (5.00 g, 30.1 mmol) in tetrahydrofuran (50 mL) at −78° C. and stirred at room temperature for 4 hours. After addition of an aqueous saturated ammonium chloride solution, the mixture was extracted with ethyl acetate, washed with saturated brine and then dried over sodium sulfate. The solvent was concentrated under reduced pressure to obtain 2,4,5-trimethyl-4,5,6-trihydrocyclopenta[1,2-b]thiophen-4-ol (5.18 g, 95%). The obtained 2,4,5-trimethyl-4,5,6-trihydrocyclopenta[1,2-b]thiophen-4-ol was dissolved in tetrahydrofuran (50 mL) and 3% hydrochloric acid (15 mL) was added at room temperature. The mixture was then stirred for 3 hours. The reaction mixture was separated by addition of toluene and water. An organic layer was washed with water and saturated brine and then dried over magnesium sulfate. The solvent was concentrated under reduced pressure to quantitatively obtain 2,4,5-trimethyl-6-hydrocyclopenta[1,2-b]thiophene.

$^1$H-NMR (deuterated chloroform, δ(ppm)): 1.97(s, 3H), 1.98(s, 3H), 2.50(s, 3H), 3.16(s, 2H), 6.58(s, 1H)

$^{13}$C-NMR (deuterated chloroform, δ(ppm)): 12.23, 14.64, 16.62, 40, 83, 116.94, 130.81, 136.38, 137.95, 142.32, 153.31.

Mass spectra (EI, m/z): 164(M$^+$), 149, 134, 115, 51, 39, 27

Example 97

Synthesis of 2,5-dimethyl-6-hydrocyclopenta[1,2-b]thiophene

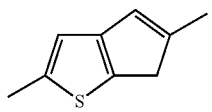

Under nitrogen atmosphere, lithium aluminum hydride (5.80 g, 66.0 mmol) and dry diethyl ether (53 mL) were loaded and a solution of 2,5-dimethyl-5,6-dihydrocyclopenta[1,2-b]thiophen-4-one (22.0 g, 132.2 mmol) in dry tetrahydrofuran (44 mL) was added dropwise thereto in an ice bath. The mixture was then stirred at room temperature for 3 hours. Then, an aqueous saturated ammonium chloride solution was added to the reaction mixture and it was extracted with ethyl acetate to obtain an organic layer. The organic layer was washed with saturated brine and dried over anhydrous magnesium sulfate. The solvent was distilled off under reduced pressure to obtain 2,5-dimethyl-4, 5,6-trihydrocyclopenta[1,2-b]thiophen-4-ol (22.5 g, 99%) as a pale yellow oil.

The obtained 2,5-dimethyl-4,5,6-trihydrocyclopenta[1,2-b]thiophen-4-ol (22.2 g, 66.0 mmol) and toluene (200 mL) were loaded, and p-toluenesulfonic acid monohydrate (804 mg) and molecular sieves 3A (10 g) were added. The mixture was then stirred at 95 to 100° C. for 1 hour. Then, water was added to the reaction mixture and it was extracted with ethyl acetate to obtain an organic layer. The organic layer was washed with saturated brine and dried over anhydrous magnesium sulfate. The solvent was distilled off under reduced pressure to obtain a pale yellow oil (19.6 g). The oil was purified by silica gel column chromatography (hexane) to obtain 2,5-dimethyl-6-hydrocyclopenta[1,2-b]thiophene (15.6 g, 79%) as a white solid.

$^1$H-NMR (deuterated chloroform, δ(ppm)): 1.82(s, 3H), 2.27(s, 3H), 2.83(s, 2H), 6.28(s, 1H), 6.52(s, 1H) $^{13}$C-NMR (deuterated chloroform, δ(ppm)): 15.80, 16.75, 40, 12, 117.69, 123.66, 137.67, 141,64, 145.80, 150.12

«Propylene Homopolymerization»

Example 98

<Polymerization Condition E-1>

An autoclave was charged with toluene (5.0 mL) under nitrogen atmosphere and the temperature was stabilized at 40° C. It was then charged with propylene until it was pressurized to 0.20 MPa, and the pressure was stabilized. Thereto MMAO (5.8% by weight of Al, Tosoh Akzo Corporation) (100 μmol) and the Complex 4 (0.10 μmol) were added to carry out polymerization for 30 min. As a result of polymerization, a polymer having the molecular weight (Mw)=248,000, the molecular weight distribution (Mw/Mn)=1.5 and Tm=116.6° C. was produced in an amount of 1.9×10$^6$ g per 1 mol of titanium and per an hour.

Example 99

<Polymerization Condition F-1>

An autoclave was charged with toluene (5.0 mL) under nitrogen atmosphere and the temperature was stabilized at 40° C. It was then charged with propylene until it was pressurized to 0.20 MPa, and the pressure was stabilized. Thereto a solution of triisobutylaluminum in hexane (40 μL, 1.0 M, Kanto Chemical Co., Ltd.), pentafluorophenylborane (0.30 μmol) and the Complex 4 (0.10 μmol) were added to carry out polymerization for 30 min. As a result of polymerization, a polymer was produced in an amount of 1.0×10$^5$ g per 1 mol of titanium and per an hour.

Example 100

<Polymerization Condition Ge1>

An autoclave was charged with toluene (5.0 mL) under nitrogen atmosphere and the temperature was stabilized at 40° C. It was then charged with propylene until it was pressurized to 0.20 MPa, and the pressure was stabilized. Thereto a solution of triisobutylaluminum in hexane (40 μL, 1.0 M, Kanto Chemical Co., Ltd.), dimetylanilinium tetrakis (pentafluorophenyl)borate (0.30 μmol) and the Complex 4 (0.10 μmol) were added to carry out polymerization for 30 min. As a result of polymerization, a polymer having the molecular weight (Mw)=491,000, the molecular weight distribution (Mw/Mn)=1.7 and Tm=104.4° C. was produced in an amount of 16.9×10$^6$ g per 1 mol of titanium and per an hour.

Example 101

<Polymerization Condition H-1>

An autoclave was charged with toluene (5.0 mL) under nitrogen atmosphere and the temperature was stabilized at 40° C. It was then charged with propylene until it was pressurized to 0.20 MPa, and the pressure was stabilized. Thereto a solution of triisobutylaluminum in hexane (40 μL, 1.0 M, Kanto Chemical Co., Ltd.), triphenylmethyl tetrakis (pentafluorophenyl)borate (0.30 μmol) and the Complex 4 (0.10 μmol) were added to carry out polymerization for 30 min. As a result of polymerization, a polymer having the molecular weight (Mw)=527,000, the molecular weight distribution (Mw/Mn)=1.64 and Tm=113.4° C. was produced in an amount of 16.1×10$^6$ g per 1 mol of titanium and per an hour.

«Copolymerization of Ethylene/1-Butene»

Example 102

<Polymerization Condition I-1>

After a flask was charged with toluene (1.0 L) under nitrogen atmosphere, ethylene (8.0 L/min) and 1-butene (2.0 L/min) were blown thereinto respectively and the temperature was stabilized at 30° C. Thereto a solution of triisobutylaluminum in hexane (0.5 mL, 1.0 M, Kanto Chemical Co., Ltd.), the Complex 4 (0.5 μmol) and dimethylanilinium tetrakis(pentafluorophenyl)borate (0.5 μmol) were added to carry out polymerization for 60 min. As a result of polymerization, a polymer having the molecular weight (Mw)=292,000 and the molecular weight distribution (Mw/Mn)=1.43 was produced in an amount of 4.3×10$^6$ g per 1 mol of titanium and per an hour.

Example 103

Polymerization was carried out in the same manner as Example 102, except that the Complex 5 was used. As a result of polymerization, a polymer having the molecular weight (Mw)=15,000 and the molecular weight distribution (Mw/Mn)=1.46 was produced in an amount of 10.5×10$^6$ g per 1 mol of titanium and per an hour.

«Copolymerization of Propylene/1-Butene»

Example 104

<Polymerization Condition J-1>

After a flask was charged with toluene (1.0 L) under nitrogen atmosphere, propylene (8.0 L/min) and 1-butene (2.0 L/min) were blown thereinto respectively and the temperature was stabilized at 30° C. Thereto a solution of triisobutylaluminum in hexane (0.5 mL, 1.0 M, Kanto Chemical Co., Ltd.), the Complex 4 (0.5 μmol) and dimethylanilinium tetrakis(pentafluorophenyl)borate (0.5 μmol) were added to carry out polymerization for 60 min. As a result of polymerization, a polymer having the molecular weight (Mw)=297,000 and the molecular weight distribution (Mw/Mn)=1.47 was produced in an amount of 2.0×10⁶ g per 1 mol of titanium and per an hour.

Example 105

Polymerization was carried out in the same manner as Example 104, except that the Complex 5 was used. As a result of polymerization, a polymer having the molecular weight (Mw)=763,000 and the molecular weight distribution (Mw/Mn)=1.45 was produced in an amount of 4.5×10⁶ g per 1 mol of titanium and per an hour.

«Copolymerization of Ethylene/Styrene/Norbornene»

Example 106

<Polymerization Condition K-1>
An autoclave was charged with toluene (100 mL), styrene (200 mmol) and norbornene (200 mmol) under nitrogen atmosphere. The autoclave was then charged with ethylene until it was pressurized to 0.4 MPa, and the temperature was stabilized at 50° C. Thereto a solution of triisobutylaluminum in hexane (1.0 mL, 1.0 M, Kanto Chemical Co., Ltd.), the Complex 4 (5.0 µmol) and dimethylanilinium tetrakis (pentafluorophenyl)borate (10.0 µmol) were added to carry out polymerization for 60 min. As a result of polymerization, a polymer was produced in an amount of 5.3×10⁶ g per 1 mol of titanium and per an hour.

Example 107

<Polymerization Condition K-2>
An autoclave was charged with toluene (150 mL), styrene (300 mmol) and norbornene (300 mmol) under nitrogen atmosphere. The autoclave was then charged with ethylene until it was pressurized to 0.4 MPa, and the temperature was stabilized at 50° C. Thereto a solution of triisobutylaluminum in hexane (1.5 mL, 1.0 M, Kanto Chemical Co., Ltd.), the Complex 5 (7.5 µmol) and dimethylanilinium tetrakis (pentafluorophenyl)borate (15.0 µmol) were added to carry out polymerization for 60 min. As a result of polymerization, a polymer was produced in an amount of 5.0×10⁶ g per 1 mol of titanium and per an hour.

«High Temperature and High Pressure Polymerization»

Example 108

<Polymerization Condition L-1>
An autoclave was charged with cyclohexane (185 mL) and 1-hexene (15 mL) under nitrogen atmosphere and the temperature was stabilized at 180° C. It was then charged with ethylene until it was pressurized to 2.50 MPa, and the pressure was stabilized. Thereto triisobutylaluminum (0.30 mmol), dimethylanilinium tetrakis(pentafluorophenyl)borate (3.0 µmol) and the Complex 5 (0.50 µmol) were added to carry out polymerization for 2 min. As a result of polymerization, a polymer having the molecular weight (Mw)=113,500 and the molecular weight distribution (Mw/Mn)=1.8 was produced in an amount of 21.5×10⁷ g per 1 mol of titanium and per an hour.

The following Table 6 shows the catalytic components, polymerization conditions, catalytic activity, reaction results of Examples 108 to 111 and those in Comparative Example 10 using dimethylsilyl(tetramethylcyclopentadienyl)(3-tert-butyl-5-methyl-2-phenoxy)titanium dimethoxide [Complex 8].

TABLE 6

[Complex 8]

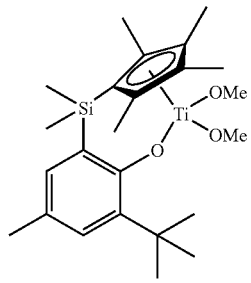

Ethylene/1-hexene copolymerization (TIBA/AB)

| Example | Complex | Polymerization condition | Temperature (° C.) | Activity*¹ | Mw | Mw/Mn | SCB*² |
|---|---|---|---|---|---|---|---|
| 108 | 5 | L-1 | 180 | 21.5 | 113,500 | 1.8 | 24.7 |
| 109 | 3 | L-1 | 180 | 21.4 | 83,000 | 2.0 | 22.6 |
| 110 | 2 | L-1 | 180 | 24.1 | 74,700 | 1.8 | 20.3 |
| 111 | 1 | L-1 | 180 | 8.2 | 88,500 | 1.7 | 11.8 |

| Comparative Example | Complex | Polymerization condition | Temperature (° C.) | Activity*¹ | Mw | Mw/Mn | SCB*² |
|---|---|---|---|---|---|---|---|
| 10 | 8 | L-1 | 180 | 13.1 | 52,600 | 2.1 | 34.5 |

*¹(×10⁷ gPE/mol-cat/hr)
*²The number of branched methyl groups per 1,000 carbon atoms of a polymer.

Example 112

Synthesis of (2-allyloxy-3-tert-butyl-5-methylphenyl)(cyclopenta[1,2-b:4,3-b']dithiophen-7-yl)diethylsilane

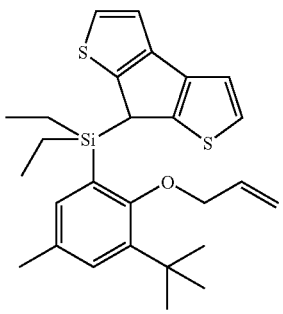

To a solution of cyclopenta[1,2-b:4,3-b']dithiophene (0.50 g, 280 mmol) in tetrahydrofuran (25 mL) was added dropwise n-butyllithium (1.56 M, 1.88 mL, 2.94 mmol) at −78° C. and stirred at room temperature for 4 hours. The mixture was cooled to −78° C. and a solution of (2-allyloxy-3-tert-buyl-5-methylphenyl)chlorodimethylsilane (0.83 g, 2.80 mmol) in toluene (5 mL) was added dropwise thereto. The resulting reaction mixture was warmed to room temperature and stirred for 2 hours. After the solvent was distilled off under reduced pressure, toluene was added and the mixture was filtered to remove insoluble substances. The filtrate was concentrated under reduced pressure to quantitatively obtain (2-allyloxy-3-tert-butyl-5-methylphenyl)(cyclopenta[1,2-b:4,3-b']dithiophen-7-yl)diethylsilane.

$^1$H-NMR (deuterated benzene, δ(ppm)): 0.67–0.96(m, 10H), 1.51(s, 9H), 2.23(s, 3H), 4.33–4.35(m, 2H), 4.49(s, 1H), 4.99–5.04(m, 1H), 5.43–5.55(m, 1H), 5.67–5.78(m, 1H), 6.93(d, J=5.0 Hz, 2H), 7.03(d, J=5.0 Hz, 2H), 7.20(s, 1H), 7.34(s, 1H).

Example 113

Synthesis of diethylsilyl(2,5-dimethylcyclopenta[1,2-b:4,3-b']dithiophen-7-yl)(3-tert-butyl-5-methyl-2-phenoxy)titanium dichloride [Complex 9]

[Complex 9]

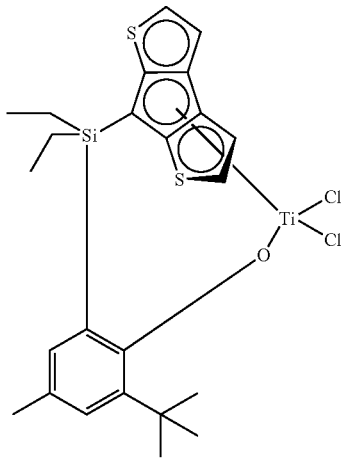

A 1.56 M solution of n-butyllithium in hexane (3.78 mL, 5.9 mmol) was added dropwise to a solution of (2-allyloxy-3-tert-butyl-5-methylphenyl)(cyclopenta[1,2-b:4,3-b']dithiophen-7-yl)diethylsilane (1.23 g, 2.6 mmol) and triethylamine (1.20 g, 11.9 mmol) in toluene (15.0 mL) at −78° C. and stirred for 10 minutes and then at room temperature for 2 hours. A solution of titanium tetrachloride (0.75 g, 4.0 mmol) in toluene (4.0 mL) was added dropwise at −78° C. to the reaction mixture and the mixture was stirred at room temperature for 5 hours. The reaction mixture was concentrated and filtered using hexane to remove insoluble substances. After the solvent was distilled off under reduced pressure, the residue was washed with pentane to obtain diethylsilyl(cyclopenta[1,2-b:4,3-b']dithiophen-7-yl)(3-tert-butyl-5-methyl-2-phenoxy)titanium dichloride (137.5 mg, 9.6%) as a reddish brown solid.

$^1$H-NMR (deuterated benzene, δ(ppm)): 0.81–1.03(m, 6H), 1.16–1.27(m, 4H), 1.46(s, 9H), 2.21(s, 3H), 6.80(d, J=5.5 Hz, 2H), 6.91(d, J=5.5 Hz, 2H), 7.22(s, 1H), 7.25(s, 1H).

Mass spectra (EI, m/z): 542 (M$^+$), 513, 491, 275

INDUSTRIAL APPLICABILITY

High molecular weight polyolefin can be produced with high catalytic activity by using a transition metal complex obtained according to the present invention as a catalytic component.

The invention claimed is:
1. A transition metal complex represented by the following formula (1):

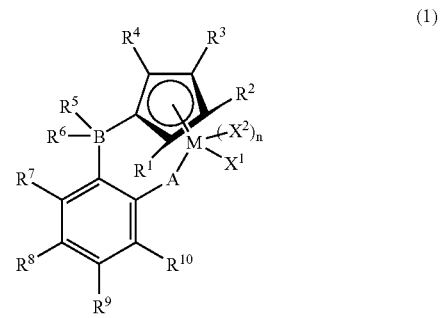

(1)

wherein M is a Group 4 transition metal;
A is a Group 16 element;
B is a Group 14 element;
n is an integer of 0 or 1;
R$^1$, R$^2$, R$^3$ and R$^4$ are the same or different and each independently denotes a substituent selected from the group consisting of the following groups (I) and (II):
group (I) consisting of
hydrogen,
substituted or unsubstituted C$_{1-20}$ alkyl,
substituted or unsubstituted C$_{6-20}$ aryl,
substituted or unsubstituted C$_{7-20}$ aralkyl, and
silyl substituted with substituted or unsubstituted C$_{1-20}$ hydrocarbon, and
group (II) consisting of
substituted or unsubstituted C$_{1-20}$ alkoxyl,
substituted or unsubstituted C$_{6-20}$ aryloxy,
substituted or unsubstituted C$_{7-20}$ aralkyloxy,
silyloxy substituted with substituted or unsubstituted C$_{1-20}$ hydrocarbon,
amino substituted with substituted or unsubstituted C$_{1-20}$ hydrocarbon, phosphino substituted with substituted or unsubstituted C$_{1-20}$ hydrocarbon, and thio substituted with substituted or unsubstituted C$_{1-20}$ hydrocarbon, provided that at least one of R$^1$, R$^2$, R$^3$ and R$^4$ is a substituent selected from the group (II);

R$^5$, R$^6$, R$^7$, R$^8$, R$^9$ and R$^{10}$ are the same or different and each independently denotes hydrogen, halogen, substituted or unsubstituted C$_{1-20}$ alkyl, substituted or unsubstituted C$_{1-20}$ alkoxy, substituted or unsubstituted C$_{6-20}$ aryl, substituted or unsubstituted C$_{6-20}$ aryloxy, substituted or unsubstituted C$_{7-20}$ aralkyl, substituted or unsubstituted C$_{7-20}$ aralkyloxy, silyl substituted with substituted or unsubstituted C$_{1-20}$ hydrocarbon, or amino substituted with substituted or unsubstituted C$_{1-20}$ hydrocarbon;

X$^1$ and X$^2$ are the same or different and each independently denotes hydrogen, halogen, substituted or unsubstituted C$_{1-20}$ alkyl, substituted or unsubstituted C$_{1-20}$ alkoxy, substituted or unsubstituted C$_{6-20}$ aryl, substituted or unsubstituted C$_{6-20}$ aryloxy, substituted or unsubstituted C$_{7-20}$ aralkyl, substituted or unsubstituted C$_{7-20}$ aralkyloxy, or amino substituted with substituted or unsubstituted C$_{1-20}$ hydrocarbon; or two adjacent substituents of R$^1$, R$^2$, R$^3$ and R$^4$, and two adjacent substituents of R$^5$, R$^6$, R$^7$, R$^8$, R$^9$ and R$^{10}$ may be each optionally bonded to form a ring.

2. The transition metal complex according to claim 1, wherein one or two of R$^1$, R$^2$, R$^3$ and R$^4$ are substituted or unsubstituted C$_{1-20}$ alkoxyl, substituted or unsubstituted C$_{6-20}$ aryloxy, substituted or unsubstituted C$_{7-20}$ aralkyloxy, silyloxy substituted with substituted or unsubstituted C$_{1-20}$ hydrocarbon, amino substituted with substituted or unsubstituted C$_{1-20}$ hydrocarbon, phosphino substituted with substituted or unsubstituted C$_{1-20}$ hydrocarbon, or thio substituted with substituted or unsubstituted C$_{1-20}$ hydrocarbon.

3. The transition metal complex according to claim 1, wherein one or two of R$^1$, R$^2$, R$^3$ and R$^4$ are amino substituted with substituted or unsubstituted C$_{1-20}$ hydrocarbon or thio substituted with substituted or unsubstituted C$_{1-20}$ hydrocarbon.

4. The transition metal complex according to claim 1, wherein one or two of R$^1$, R$^2$, R$^3$ and R$^4$ are amino substituted with substituted or unsubstituted C$_{1-20}$ hydrocarbon.

5. The transition metal complex according to claim 1, wherein R$^1$, R$^2$, R$^3$ and R$^4$ are bonded to one another to form at least one thiophene ring.

6. The transition metal complex according to claim 1, which is represented by the formula (7):

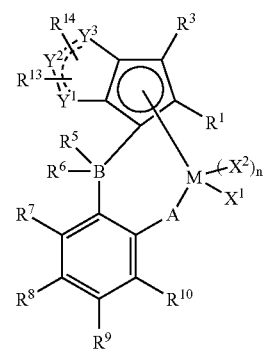

(7)

wherein M, A, B, R$^1$, R$^2$, R$^5$, R$^6$, R$^7$, R$^8$, R$^9$, R$^{10}$, X$^1$, X$^2$ and n are as defined for the formula (1);

R$^{13}$ and R$^{14}$ independently denote a substituent selected from the group (I); and the bond moiety represented by

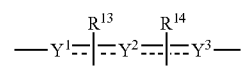

is a partial structure represented by the formula (7a):

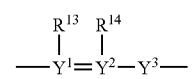

(7a)

wherein Y$^1$ and Y$^2$ are independently a carbon atom and Y$^3$ is a sulfur atom, or by the formula (7b):

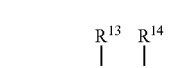

(7b)

wherein Y$^1$ is a sulfur atom and Y$^2$ and Y$^3$ are independently a carbon atom.

7. The transition metal complex according to claim 6, which is represented by the formula (8):

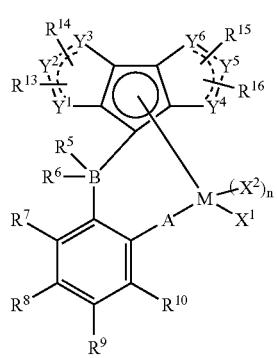

(8)

wherein M, A, B, $R^5$, $R^6$, $R^7$, $R^8$, $R^9$, $R^{10}$, $R^{13}$, $X^1$, $X^2$, $Y^1$, $Y^2$, $Y^3$, $R^{13}$, $R^{14}$, the dotted line and n are as defined for the formulas (1) and (7);
$R^{15}$ and $R^{16}$ independently denote a substituent selected from the group (I); and
the bond moiety represented by

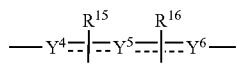

is a partial structure represented by the formula (8a):

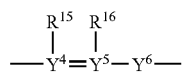
(8a)

wherein $Y^4$ and $Y^5$ are independently a carbon atom, $Y^6$ is a sulfur atom and $R^{17}$ denotes a substituent selected from the group (I), or by the formula (8b):

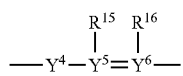
(8b)

wherein $Y^4$ is a sulfur atom and $Y^5$ and $Y^6$ are independently a carbon atom.

8. The transition metal complex according to claim 1, wherein A is an oxygen atom.

9. The transition metal complex according to claim 1, wherein B is a silicon atom.

10. The transition metal complex according to claim 1, wherein $R^{10}$ is substituted or unsubstituted $C_{1-20}$ alkyl, substituted or unsubstituted $C_{7-20}$ aralkyl, substituted or unsubstituted $C_{6-20}$ aryl, or silyl substituted with substituted or unsubstituted $C_{1-20}$ hydrocarbon.

11. The transition metal complex according to claim 1, wherein n is 1.

12. The transition metal complex according to claim 1, wherein M is titanium.

13. The transition metal complex according to claim 1, wherein $X^1$ or $X^2$ is a chlorine atom.

14. A process of producing a transition metal complex according to claim 1, which comprises reacting substituted cyclopentadiene represented by the formula (2):

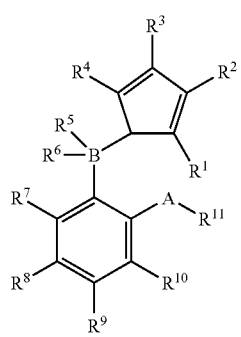
(2)

wherein A is a Group 16 element; B is a Group 14 element;
$R^1$, $R^2$, $R^3$ and $R^4$ are the same or different and each independently denotes a substituent selected from the group consisting of the following groups (I) and (II):
group (I) consisting of
hydrogen,
substituted or unsubstituted $C_{1-20}$ alkyl,
substituted or unsubstituted $C_{6-20}$ aryl,
substituted or unsubstituted $C_{7-20}$ aralkyl, and
silyl substituted with substituted or unsubstituted $C_{1-20}$ hydrocarbon, and
group (II) consisting of
substituted or unsubstituted $C_{1-20}$ alkoxyl,
substituted or unsubstituted $C_{6-20}$ aryloxy,
substituted or unsubstituted $C_{7-20}$ aralkyloxy,
silyloxy substituted with substituted or unsubstituted $C_{1-20}$ hydrocarbon,
amino substituted with substituted or unsubstituted $C_{1-20}$ hydrocarbon,
phosphino substituted with substituted or unsubstituted $C_{1-20}$ hydrocarbon, and
thio substituted with substituted or unsubstituted $C_{1-20}$ hydrocarbon,
provided that at least one of $R^1$, $R^2$, $R^3$ and $R^4$ is a substituent group selected from the group (II);
$R^5$, $R_6$, $R^7$, $R^8$, $R^9$ and $R^{10}$ are the same or different and each independently denotes hydrogen, halogen,
substituted or unsubstituted $C_{1-20}$ alkyl,
substituted or unsubstituted $C_{1-20}$ alkoxy,
substituted or unsubstituted $C_{6-20}$ aryl,
substituted or unsubstituted $C_{6-20}$ aryloxy,
substituted or unsubstituted $C_{7-20}$ aralkyl,
substituted or unsubstituted $C_{7-20}$ aralkyloxy,
silyl substituted with substituted or unsubstituted $C_{1-20}$ hydrocarbon, or
amino substituted with substituted or unsubstituted $C_{1-20}$ hydrocarbon; or
two adjacent substituents of $R^1$, $R^2$, $R^3$ and $R^4$, and two adjacent substituents of $R^5$, $R^6$, $R^7$, $R^8$, $R^9$ and $R_{10}$ may be each optionally bonded to form a ring;
$R^{11}$ is a substituted or unsubstituted hydrocarbon group or a tri-substituted silyl group; and the positions of the double bonds on the cyclopentadiene ring are optional or may be a mixture of optional positions; with a base and then reacting with a transition metal compound represented by the formula (3):

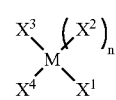
(3)

wherein M is a Group 4 transition metal; n is an integer of 0 or 1; and
$X^1$, $X^2$, $X^3$ and $X^4$ are the same or different and each independently denotes hydrogen, halogen,
substituted or unsubstituted $C^{1-20}$ alkyl,
substituted or unsubstituted $C_{1-20}$ alkoxy,
substituted or unsubstituted $C_{6-20}$ aryl,
substituted or unsubstituted $C_{6-20}$ aryloxy,
substituted or unsubstituted $C_{7-20}$ aralkyl,
substituted or unsubstituted $C_{7-20}$ aralkyloxy, or
amino substituted with substituted or unsubstituted $C_{1-20}$ hydrocarbon.

15. A catalyst for olefin polymerization comprising a transition metal complex according to claim 1 in combination with the following compound (A), wherein (A) is any one of or a mixture of two or three of the following compounds (A1) to (A3):
- (A1): an organoaluminum compound represented by the formula $E1_aAl(Z)_{(3-a)}$,
- (A2): cyclic aluminoxane having the structure represented by the formula $\{-Al(E2)-O-\}_b$,
- (A3): linear aluminoxane having the structure represented by the formula $E3\{-Al(E3)-O-\}_cAl(E3)_2$, wherein E1 to E3 are the same or different and each independently denotes a $C_{1-8}$ hydrocarbon group, Z is the same or different and each denotes hydrogen or halogen, a is an integer of 1, 2 or 3, b is an integer of 2 or more, and c is an integer of 1 or more.

16. A catalyst for olefin polymerization comprising a transition metal complex according to claim 1 in combination with the following compounds (A) and (B), wherein (A) is any one of or a mixture of two or three of the following compounds (A1) to (A3):
- (A1): an organoaluminum compound represented by the formula $E1_aAl(Z)_{(3-a)}$,
- (A2): cyclic aluminoxane having the structure represented by the formula $\{-Al(E2)-O-\}_b$,
- (A3): linear aluminoxane having the structure represented by the formula $E3\{-Al(E3)-O-\}_cAl(E3)_2$, wherein E1 to E3 are the same or different and each independently denotes a $C_{1-8}$ hydrocarbon group, Z is the same or different and each denotes hydrogen or halogen, a is an integer of 1, 2 or 3, b is an integer of 2 or more, and c is an integer of 1 or more, and (B) is any one of or a mixture of two or three of the following compounds (B1) to (B3):
- (B1): a boron compound represented by the formula BQ1Q2Q3,
- (B2): a boron compound represented by the formula $Z^+(BQ1Q2Q3Q4)^-$,
- (B3): a boron compound represented by the formula $(L-H)^+(BQ1Q2Q3Q4)^-$, wherein B is a boron atom in a trivalent valence state, Q1 to Q4 are the same or different and each is a halogen atom, a $C_{1-20}$ hydrocarbon group, a $C_{1-20}$ halogenated hydrocarbon group, a substituted silyl group having 1 to 20 carbon atoms, a $C_{1-20}$ alkoxy group or a disubstituted amino group having 2–20 carbon atoms, $Z^+$ is an inorganic or organic cation, and L-H is a Brønsted acid.

17. A process of producing an olefin polymer which comprises polymerizing olefin in the presence of the catalyst for olefin polymerization according to claim 15.

18. The process of producing an olefin polymer according to claim 17, wherein polymerization of olefin is carried out at the polymerization temperature range of −50° C. to 250° C. and under a polymerization pressure from atmospheric pressure to 10 MPa.

* * * * *